United States Patent
Granier et al.

(10) Patent No.: US 10,220,387 B2
(45) Date of Patent: Mar. 5, 2019

(54) MODULAR INSTRUMENTATION FOR ANALYZING BIOLOGICAL FLUIDS

(71) Applicant: The General Hospital Corporation, Boston, MA (US)

(72) Inventors: Robert Granier, Boston, MA (US); Ramin Haghgooie, Arlington, MA (US); Ken Kotz, Auburndale, MA (US); Anne C. Petrofsky, Sudbury, MA (US); Ronald G. Tompkins, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/101,061

(22) PCT Filed: Dec. 5, 2014

(86) PCT No.: PCT/US2014/068941
§ 371 (c)(1),
(2) Date: Jun. 2, 2016

(87) PCT Pub. No.: WO2015/085262
PCT Pub. Date: Jun. 11, 2015

(65) Prior Publication Data
US 2016/0303563 A1      Oct. 20, 2016

Related U.S. Application Data

(60) Provisional application No. 61/912,224, filed on Dec. 5, 2013, provisional application No. 62/064,846, filed on Oct. 16, 2014.

(51) Int. Cl.
*B01L 3/00*      (2006.01)
*G01N 35/00*    (2006.01)
(Continued)

(52) U.S. Cl.
CPC ..... *B01L 3/502715* (2013.01); *B01L 3/50273* (2013.01); *B01L 3/502738* (2013.01);
(Continued)

(58) Field of Classification Search
CPC .......... B01L 3/00; G01N 35/00; G01N 33/72; G01N 33/48; G01N 1/10; G01N 15/06; G01N 33/00
(Continued)

(56) References Cited

U.S. PATENT DOCUMENTS 6,503,757 B1    1/2003 Chow
8,380,541 B1    2/2013 Holmes
(Continued)

FOREIGN PATENT DOCUMENTS

WO         2015/065909         5/2015

OTHER PUBLICATIONS

International Search Report and Written Opinion dated Mar. 6, 2015 in International Application No. PCT/US2014/068941, 12 pgs.

*Primary Examiner* — Brian J. Sines
(74) *Attorney, Agent, or Firm* — Fish & Richardson P.C.

(57) ABSTRACT

A modular analytic system includes a base, at least one fluid sample processing module configured to be removably attached to the base, at least one fluid sample analysis module configured to be removably attached to the base, a fluid actuation module positioned on the base, a fluidic network comprising multiple fluidic channels, in which the fluid actuation module is arranged to control transport of a fluid sample between the at least one sample processing module and the at least one sample analysis module through the fluidic network, and an electronic processor, in which the electronic processor is configured to control operation of the fluid actuation module and receive measurement data from the at least one fluid sample analysis module.

12 Claims, 33 Drawing Sheets

(51) Int. Cl.
*G01N 1/10* (2006.01)
*G01N 15/06* (2006.01)
*G01N 21/01* (2006.01)
*G01N 21/53* (2006.01)
*G01N 15/14* (2006.01)
*G01N 21/64* (2006.01)
*G01N 15/00* (2006.01)
*G01N 15/10* (2006.01)

(52) U.S. Cl.
CPC ......... *G01N 15/1434* (2013.01); *G01N 21/01* (2013.01); *G01N 21/532* (2013.01); *G01N 21/6486* (2013.01); *G01N 35/00029* (2013.01); *G01N 35/00871* (2013.01); *B01L 2200/027* (2013.01); *B01L 2200/028* (2013.01); *B01L 2200/0689* (2013.01); *B01L 2300/0627* (2013.01); *B01L 2300/0816* (2013.01); *B01L 2300/0832* (2013.01); *B01L 2300/0861* (2013.01); *B01L 2400/0487* (2013.01); *G01N 2015/0065* (2013.01); *G01N 2015/1006* (2013.01); *G01N 2021/6493* (2013.01); *G01N 2035/00158* (2013.01); *G01N 2035/00326* (2013.01); *G01N 2035/00356* (2013.01); *G01N 2035/00881* (2013.01); *G01N 2201/062* (2013.01); *G01N 2201/06113* (2013.01)

(58) Field of Classification Search
USPC ......... 422/68.1, 502, 503, 504; 436/43, 180, 436/63, 66, 174
See application file for complete search history.

(56) References Cited

U.S. PATENT DOCUMENTS

| | | | |
|---|---|---|---|
| 8,435,738 B2 | 5/2013 | Holmes | |
| 2004/0063221 A1 | 4/2004 | Millstein | |
| 2006/0192940 A1 | 8/2006 | Phi-Wilson | |
| 2013/0115607 A1 | 5/2013 | Nielsen et al. | |
| 2013/0203634 A1 | 8/2013 | Jovanovich et al. | |
| 2013/0280699 A1 | 10/2013 | Minter et al. | |
| 2013/0316355 A1* | 11/2013 | Dryga | C07K 16/1267 435/6.12 |
| 2014/0170645 A1* | 6/2014 | Jovanovich | G01N 35/00029 435/6.11 |
| 2015/0285731 A1 | 10/2015 | Haghgooie et al. | |

* cited by examiner

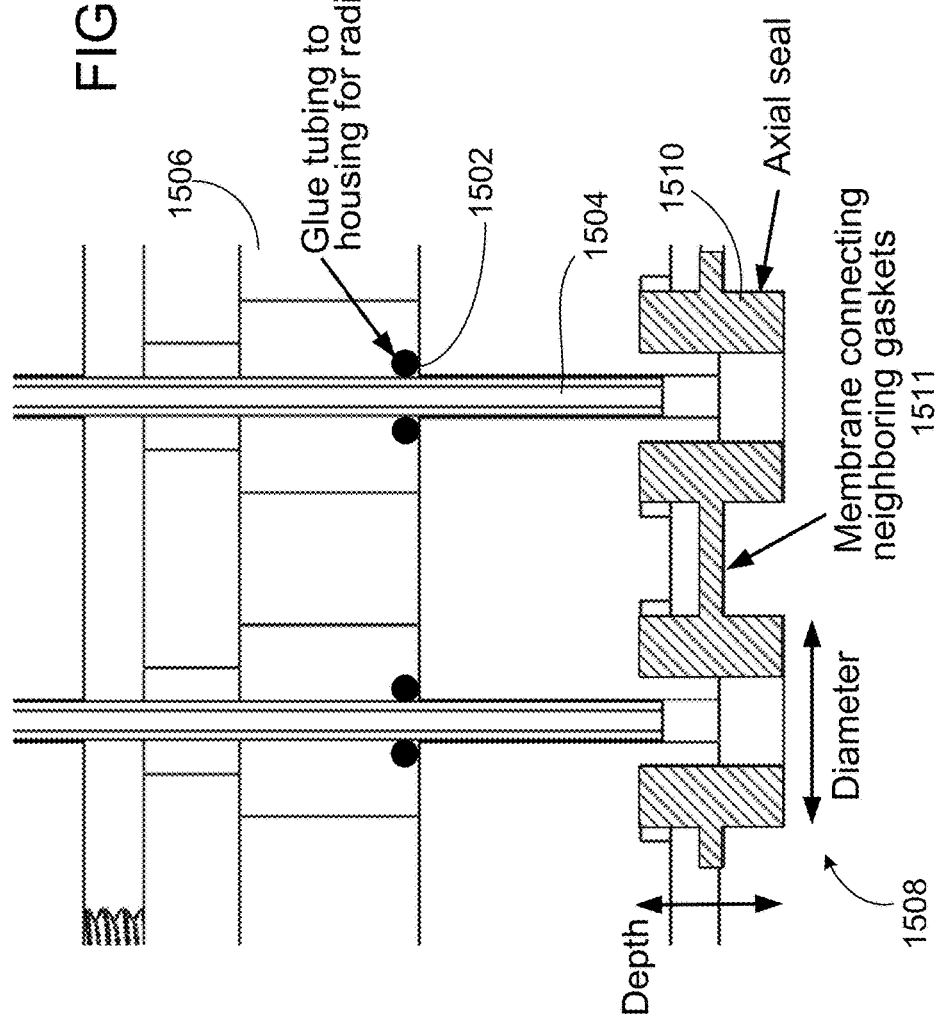

MODULAR INSTRUMENTATION FOR ANALYZING BIOLOGICAL FLUIDS

CROSS-REFERENCE TO RELATED APPLICATION

This application is a 371 application of International Application No. PCT/US2014/068941, filed on Dec. 5, 2014, which claims the benefit of U.S. Provisional Application No. 61/912,224, filed on Dec. 5, 2013, and U.S. Provisional Application No. 62/064,846, filed on Oct. 16, 2014. The contents of each of these applications is incorporated herein by reference in its entirety.

STATEMENT OF FEDERALLY SPONSORED RESEARCH OR DEVELOPMENT

This invention was made with Government support under U54GM062119 and P41EB002503, awarded by the National Institutes of Health. The Government has certain rights in the invention.

BACKGROUND

This disclosure relates to systems for analyzing biological fluids. In particular, this disclosure relates to an analytic system in which one or more components of the system are modular in nature and connectable to a fluidic network via standardized connectors.

As biological diagnostics have increased in complexity over the past decades, there has been a trend for diagnostics and testing equipment to be removed from points of care, such as a physician's office, and moved to centralized laboratory service locations. At least in part, this trend was due to perceived problems in quality control stemming from performing testing at various points of care with traditional diagnostic technology. For example, in comparison to a large medical center with a sizable staff of highly skilled technicians, a small town physician's office with a small independent lab was believed to lack the oversight and technical support necessary to properly operate and service complicated laboratory equipment.

Such trends have been reinforced by federal legislation and regulations, such as those imposed by the Clinical Laboratory Improvement Act (CLIA) of 1988, despite protests from physicians' organizations. From 1988 forward, many physician office laboratories were closed, as they were unable to comply with the requirements of the CLIA. As of 2011, more than 90% of all diagnostics testing was performed in centralized laboratories.

While this centralized approach may have been a solution for controlling the quality of diagnostic information considering the technology at the time, it is not without its problems. Perhaps the greatest problem is that patients in medically underserved areas, which are primarily served by physicians operating out of small or mobile offices, now had reduced access to important diagnostic testing. Test samples either needed to be collected and transported (which can present potential additional cost and handling) or patients needed to travel to a centralized laboratory facility to have tests performed (which may require that patients living in rural environments travel a great distance, which can dissuade some patients from having the test performed at all due to the cost or the time associated with travel).

Very recently, some attempts have been made to move more diagnostic testing back to or towards the point of care. However, their limited adoption reveals the many challenges of moving testing to the point of care in the current healthcare environment. Among the problems are that most current point of care solutions either significantly sacrifice quality to try to compete with centralized laboratory services on cost (for example, most lab-on-a-chip designs have a target price point that requires significant tradeoffs between cost and performance) or are not particularly economical as a whole (for example, multiple systems are required for various types of analytes and many physicians must still rely a centralized laboratory to meet at least some of their routine testing needs).

Still further, most point of care laboratories have separate systems for different diagnostic tests. At a small or medium sized testing facility, it can be hard to justify the expense of separate systems for different types of tests where testing volume is relatively low. Further, selecting a suite of efficient devices is often difficult as there is often redundant, unshared hardware across the various devices yet, due to differences in the device interfaces, middleware must still be obtained to integrate and connect the various devices into a single laboratory information system. At the same time, having multiple testing devices takes up significant laboratory real estate and can mean separate systems to operate and maintain, separate contracts to manage, and separate manufacturers and vendors. Thus, even with the high desirability of a return to point of care diagnostics testing, currently there has been very limited adoption of this model.

Hence, a need exists for improved administration of diagnostic testing. Among other things, there is a strong need for improved distribution and servicing of reliable diagnostics equipment at mid- and small-sized points of care.

SUMMARY OF THE INVENTION

The present disclosure relates to improved systems and methods for diagnostics testing. The new systems enable sophisticated and complex testing equipment to be implemented at the point of care and enable an efficient and distributed diagnostics infrastructure. By designing the analytic system to have modular components, which may be of a plug-and-play type, systems can be built that are both flexible in the types of diagnostic tests that they can perform and that are easily serviceable and/or upgradeable by the replacement of one or more of the modules. Replacement modules can be shipped or couriered to the point of care and modules that need to be repaired or serviced can be sent to a skilled technician who resides off-site. In some embodiments, one or more of the modules may be non-serviceable or disposable.

Among other things, the disclosed systems potentially permit the healthcare landscape to shift more types of testing and care back to the point of care for primary care delivery, where the testing and care might be more efficiently administered by physicians, physicians' assistants, and nurse practitioners. Even a modest shift of testing back to mid-tier laboratories, in which highly specialized labor is not required to be on-site to maintain and service diagnostics equipment, would reduce access barriers to healthcare and improve service quality. A modular analytic system of the type disclosed herein accommodates the shift to this distributed health care model by permitting more of the diagnostics testing to occur closer to or at the point of care.

Furthermore, the modular analytic systems described herein are readily employable in research laboratories, where the flexibility of the device (due to its modular nature) permits the laboratory to build its own device ala carte to include only the diagnostics modules of interest. Further, because the modular systems can accommodate plug-and-play type modules, the analytic systems can be readily rebuilt or expanded as the needs of the laboratory change. Additionally, the integration of sample capture, handling, measurement, and diagnostics in a single system that is reconfigurable depending on the desired tests to be performed can enable significant reductions in costs relative to systems that employ one or more of those features using separate platforms.

In general, in one aspect, the subject matter of the present disclosure can be embodied in a modular analytic system (or systems) that includes a base, at least one fluid sample processing module configured to be removably attached to the base, at least one fluid sample analysis module configured to be removably attached to the base, a fluid actuation module positioned on the base, a fluidic network including multiple fluidic channels, in which the fluid actuation module is arranged to control transport of a fluid sample between the at least one sample processing module and the at least one sample analysis module through the fluidic network, and an electronic processor, in which the electronic processor is configured to control operation of the fluid actuation module and receive measurement data from the at least one fluid sample analysis module.

Implementations of the system can include one or more of the following features. For example, in some implementations, the system further includes a cartridge, in which the cartridge includes: one or more first receptacles configured to store a fluid sample; one or more second receptacles configured to store a reagent; and one or more third receptacles. The fluid sample processing module can include an opening to receive the cartridge. The sample processing module further can include an actuation input port and a fluid output port, in which the actuation input port and the fluid output port are arranged to couple to the third receptacle of the cartridge when the cartridge is positioned in the opening of the sample processing module. The base can include a first connector interface coupled to the fluid actuation module, in which the actuation input port of the sample processing module is configured to mate with the first connector interface. The board can include a fluidic connector interface coupled to the fluidic network, in which the fluidic output port of the sample processing module is configured to mate with the fluidic connector interface.

In some implementations, the at least one fluid sample analysis module includes a light detector module, an electrochemistry module, a cytometry module, or a Coulter counter module.

In some implementations, the at least one fluid sample analysis module includes multiple internal tubes, in which at least one tube is arranged to receive a fluid sample from the fluidic network and at least one other tube is arranged to deliver a fluid sample to the fluidic network when the at least one fluid sample analysis module is attached to the base.

In some implementations, the system includes multiple the fluid sample analysis modules removably attached to the base, in which at least one fluid sample analysis module is arranged to deliver a fluid sample through the fluidic network to at least one other fluid sample analysis module.

In some implementations, the fluid actuation module includes a pneumatic pump or a hydraulic pump to supply pneumatic pressure or hydraulic pressure, respectively, to the fluidic network. The fluid actuation module can include a manifold that separates the pneumatic pressure or the hydraulic pressure supplied by the fluid actuation module into multiple independent channels. The fluid actuation module can include multiple valves, in which the electronic processor is operable to control the operation of the plurality of valves.

In some implementations, the fluid actuation module is removably attached to the base. The fluid actuation module can include one or more protrusions or openings, in which, for each protrusion or opening on the fluid actuation module, the base includes a corresponding opening or protrusion that frictionally fits to the protrusion or opening.

In some implementations, the system further includes a waste module configured to be removably attached to the base, in which the waste module includes a fluidic connector interface that mates with one or more of the fluidic channels. The waste module can include one or more protrusions or openings, in which, for each protrusion or opening on the waste module, the base includes a corresponding opening or protrusion that frictionally fits to the protrusion or opening. The fluidic actuation module can be operable to control the flow of fluid samples from the at least one analytic module to the waste module.

In some implementations, the fluidic channels are formed in the base.

In some implementations, the fluidic channels include multiple tubes.

In some implementations, at least one seal is between the fluidic network and the at least one fluid sample analysis module. The at least one seal can include a sealing gasket interposed between the at least one fluid sample analysis module and the fluidic network. The at least one fluid sample analysis module can include an internal tube, and the at least one seal comprises an O-ring that forms a sealed pathway between the internal tube and a corresponding fluidic channel of the fluidic network. The at least one fluid sample analysis module can include an internal tube, in which the at least one seal includes a sealing gasket interposed between the fluidic network and an exterior surface of the at least one fluid sample analysis module, and in which the internal tube extends, at least in part, through an opening in the sealing gasket to form a sealed pathway between the internal tube and a corresponding fluidic channel of the fluidic network. Compression of the sealing gasket between the fluid network and the exterior surface of the at least one fluid sample analysis module can cause the opening of the sealing gasket to compress around the internal tube.

In some implementations, each of one or more modules selected from the group consisting of the fluid sample processing modules and the fluid sample analysis modules includes a surface having at least one protrusion, and the base includes, for each protrusion, a corresponding opening that mates with the protrusion.

In some implementations, each of one or more modules selected from the group consisting of the fluid sample processing modules and the fluid sample analysis modules includes a surface having at least one opening, and the base includes, for each opening, a corresponding protrusion that mates with the opening.

In general, in another aspect, the subject matter of the disclosure can be embodied in methods that include: providing a base including a fluid sample processing module, a fluid sample analysis module, and a fluid actuation module, in which each of the fluid sample analysis module and the fluid sample processing module is removably attached to the base, and in which the fluid sample processing module and the fluid sample analysis module are coupled together through a fluidic channel network supported by the base; providing a fluid sample to the fluid sample processing module; activating the fluid actuation module so that the fluid sample is transferred from the fluid sample processing module through the fluidic channel network to the fluid sample analysis module; performing an analysis of the fluid sample in the fluid sample analysis module to obtain measurement data; and transmitting the measurement data to an electronic processor.

Implementations of the methods can include one or more of the following features. For example, in some implementations, providing the fluid sample to the fluid sample processing module includes providing the fluid sample to a cartridge including a receptacle configured to store a fluid sample, and receiving the cartridge in an opening in the fluid sample processing module. The cartridge can include a reagent, and the methods can further include mixing the fluid sample with the reagent to provide a pre-processed fluid sample. An input port of the fluid sample processing module can be coupled to the fluid actuation module through a connector interface on the base, in which an output port of the fluid sample processing module is coupled to the fluidic channel network. Activating the fluid actuation module can include supplying pneumatic or hydraulic pressure to the input port such that the pre-processed fluid sample is transported from the output port to the fluidic channel network. The methods can further include incubating the fluid sample with the reagent and/or separating the fluid sample into a plurality of aliquots.

In some implementations, activating the fluid actuation module includes operating one or more valves on a manifold to provide pneumatic pressure or hydraulic pressure to the fluid sample processing module.

In some implementations, the methods further include activating the fluid actuation module to transport the fluid sample from the fluid sample analysis module to a waste container supported by the base. The waste container can be removably attached to the base.

In some implementations, performing an analysis of the fluid sample in the fluid sample analysis module includes performing cytometry on the fluid sample, detecting a response to the application of an electromagnetic field or current to the fluid sample, performing an electrochemical reaction with the fluid sample, or imaging the fluid sample.

According to one aspect of the disclosure, a modular analytic system includes one or more sample preparation systems, one or more modular detectors, and a fluidic network (which may, in some forms, include or be a fluidic motherboard such as base 150 in FIG. 2). The fluidic network includes one or more sets of connectors for selective connection of the fluidic network to the sample preparation system(s) and one or more sets of connectors for selective connection of the fluidic network to the modular detector(s). The fluidic network places the sample preparation system(s) in fluid communication with the modular detector(s).

The modular analytic systems are flexible in their application. For example, the modular analytic systems can have a sample preparation system that is cartridge-based for point-of-care testing diagnostics in a clinical environment. Such a system may have the modular analytic system perform as an integrated bench-top clinical analyzer for performing panels of assays including hematology, clinical chemistry, urinalysis, immunoassays, and/or combinations thereof. As still another example, the sample preparation system can include a well plate and pipetting arrangement and the modular analytic system can permit an end user to develop their own assays such as may be more common in a research environment.

In some implementations, the modular analytic system includes a flow control subsystem that is integrated with the fluidic network to control the flow of fluids between the sample preparation system and the modular detector(s). The flow control subsystem can further control the flow of fluids from a mixing module to one of the modular detectors. The flow control subsystem can control the flow of fluids, e.g., using one or more of a pneumatic pump and a hydraulic pump.

One of the advantages of the modular approach described herein is that each of the modular detectors can be fully integrated and include all of the components necessary to perform one or more assays. One or more of the modular detectors can be adapted to process a multitude of independently run assays simultaneously. For example, these multiple assays can be performed in a multiplexed or parallel fashion. In still other forms of the device, multiple assays can be performed in series or multiple samples can be processed in series. As one specific example, one or more of the modular detectors can include a multiplexed photometry system. As another specific example, one or more of the modular detectors include a multi-parametric flow cytometer.

Another advantage of the modular approach described herein is that the modular analytic system is customizable and the fluidic network can be adapted to support various combinations of modular detectors. The connections between the fluid network and the modular detector(s) can be of a plug-and-play type connection in which the connection between the modular detector(s) and the fluid network provides the modular detector(s) with all of the fluidic inputs and outputs for an operation of the modular detector(s). By making the modular detectors easily replaceable, a module that requires service can be removed and a working module inserted in its place. By permitting such easy replacement of a module, a non-working module can be quickly replaced with a working module and the non-working module can be serviced at the convenience of a skilled technician or may be disposable. In contrast, many "hardwired" non-modular testing devices require a technician to come on-site to repair or service the device. This can lead to long operational downtimes in which the equipment is non-functional and cannot be utilized.

The modular analytic systems can further include a controller that communicates with and/or controls one or more of the modular detectors and/or the flow control subsystem. In some forms, the modular detector(s) include an electrical connection for communication with the controller.

With respect to the connectors, the set(s) of connectors for connecting the fluidic network to the modular detector(s) may include a plurality of tubes that place channels in the fluidic network and the modular detector(s) in fluid communication with one another. Seals can be formed between the plurality of tubes and one or more of the fluidic network and modular detector(s). The seal(s) include a sealing gasket interposed between the fluidic network and a coupling manifold or member in which the plurality of tubes extend, at least in part, through openings in the sealing gasket. The compression of the sealing gasket between the fluid network and the coupling manifold or member can cause openings of the sealing gasket to compress around the plurality of tubes to assist in forming the seal(s).

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and will be apparent from the description, drawings, and claims.

BRIEF DESCRIPTION OF THE DRAWINGS

It should be understood that the drawings are provided for the purpose of illustration only and are not intended to define the limits of the invention. The present invention is not limited to the precise arrangements and instrumentalities shown in the drawings, and the drawings are not necessarily to scale, emphasis instead being placed upon illustrating the principles disclosed herein.

FIG. 15D is a schematic that illustrates a cross-section view of a gasket seal.

DETAILED DESCRIPTION

Figure 1:
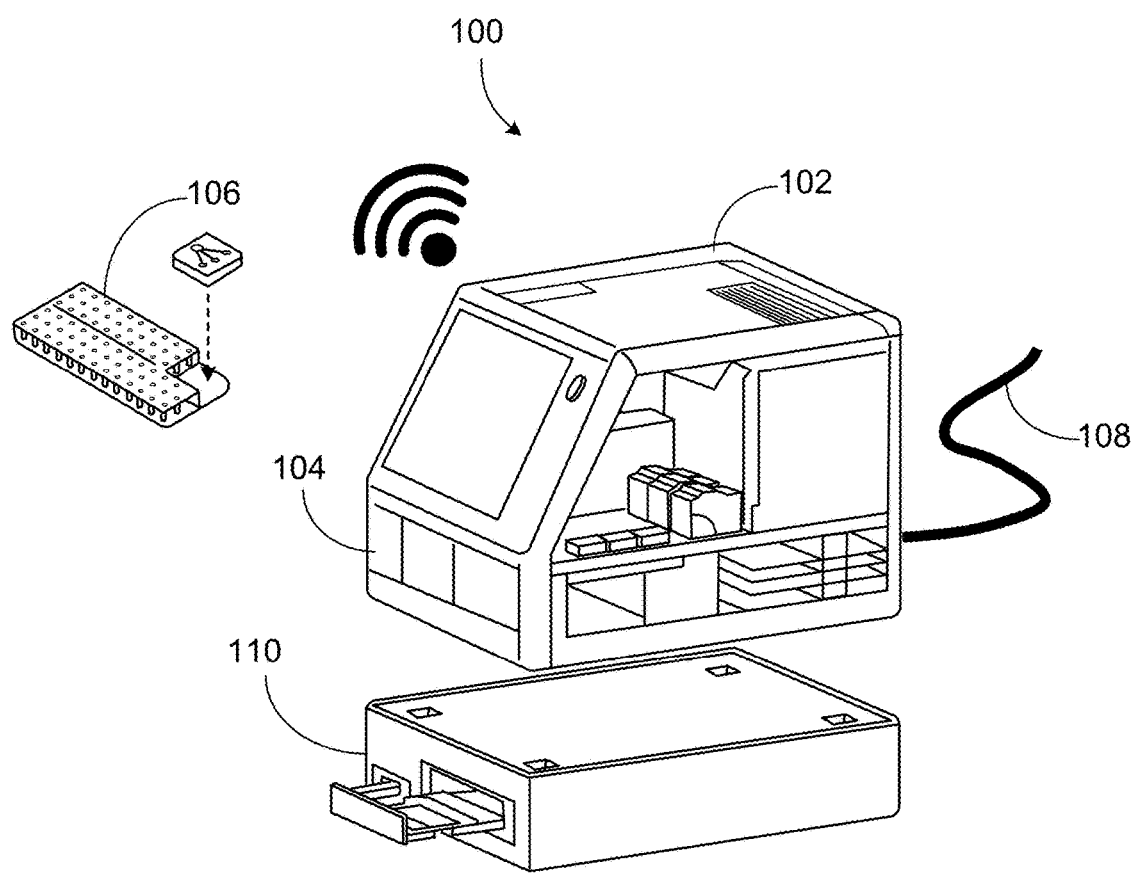
FIG. 1 is a schematic that illustrates an example of a modular analytic system as disclosed herein.

FIG. 1 shows an example of a modular analytic system 100. As illustrated, the modular analytic system 100 includes a central unit 102 which houses a fluidic network and various modular components as will be described in greater detail below.

The modular analytic system 100 is adapted to receive a number of inputs and outputs. On a front face of the central unit 102 of the modular analytic system 100, there may be a slot 104 or other type of receiving area for the selective introduction of a sample preparation unit such as the assay cartridge 106. The assay cartridge 106 may receive, contain, and store one or more samples and may receive, contain, and store one or more reagents for performing assays of the sample(s). Sample(s) may include, for example, any one of a number of types of biological fluids including, but not limited to blood, urine, saliva, and so forth. The samples and/or reagents include one or more samples and/or reagents of the same or different types. For example, multiple blood samples could be supported on a single sample preparation system and these samples could be either from the same or from different patients. As another example, different types of samples could be provided on a single cartridge (for example, blood and urine from the same patient). Unless specified in the claims, nothing in this application should be so construed as limiting the type, number, and combinations of samples and reagents that may be carried by the sample preparation system.

Although a cartridge-based system is illustrated in FIG. 1, it should be appreciated that other types of sample preparation systems may be used. Some of these alternative sample preparation systems will be described below. For example, the sample preparation system could incorporate a pipetting/well plate configuration for a more research-oriented environment. Of course, the slot 104 or means for connecting the sample preparation system to the central unit 102 of the modular analytic system 100 may be modified or adapted to accommodate a connection between whatever sample preparation system is used and the internal fluidic network and modules.

The central unit 102 may include either or both of wired connections (such as enabled by cable 108) and wireless connections (such as enabled by a wireless adapter, illustrated by wireless signal lines). For ease of use and connection, there may be a single cable 108 that connects the central unit 102 to a controller or computer and may be adapted to provide both a data connection and a power connection. Similarly, separate data and power connections may be supplied. However, it is also contemplated that there may be multiple cables for power, data, and or both.

In the form illustrated in FIG. 1, there is also a separate and optional auxiliary unit 110 that is attached to the central unit 102. In the form illustrated, the auxiliary unit 110 is adapted to perform molecular diagnostics and lateral flow assays and is in communication with the central unit 102.

Figure 2:
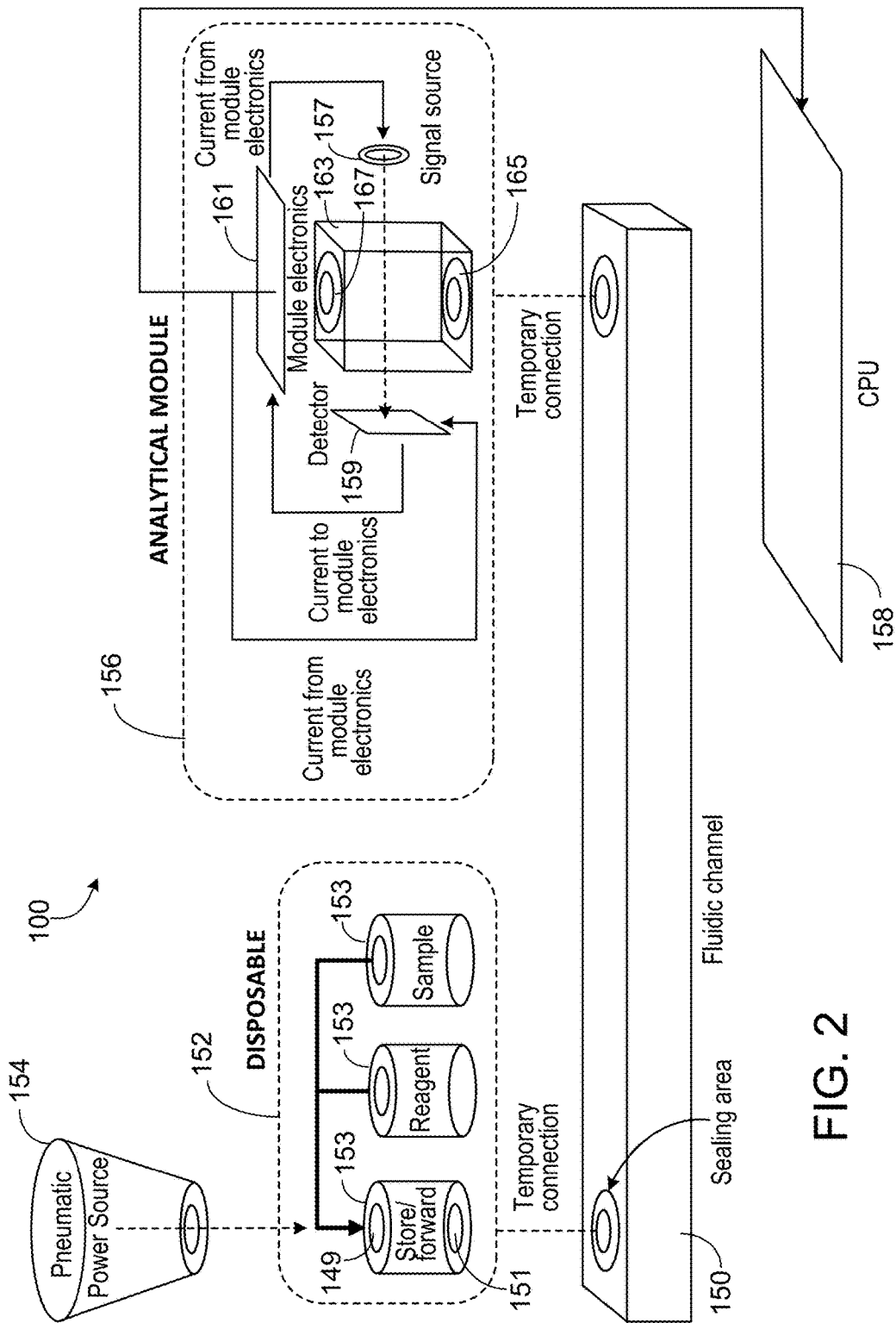
FIG. 2 is a schematic that illustrates an overview of different components of a modular analytic system.

FIG. 2 is a schematic that illustrates an overview of the different components of the modular analytic system 100 in more detail. As shown in FIG. 2, the system includes a support base 150 (also called a fluidic motherboard) that acts as a support for holding and securing together the different modular components in a single compact system. In some implementations, the base 150 also includes at least a portion of the fluidic network. The fluidic network includes multiple fluidic channels through which fluid can be transported between the different modular units of the modular analytic system 100. The fluidic channels can be formed within the base 150 and have openings and/or seals that fluidly couple to the different modular components. In some implementations, some or all of the fluidic channels are formed external to the base 150. For instance, in some cases, the fluidic channels include tubing that is coupled to the different modular components of the analytic system. The fluidic channels can be fluidly coupled and sealed to the different modular components using custom gaskets, as will be described below. In some implementations, the fluidic channels of the fluidic network are reconfigurable. That is, the particular connections that the fluidic channels make with the sample processing modules and the analytical modules may be rearranged according to different predefined configurations, such that a user can modify the modular analytical system for desired operations.

The base 150 can be composed of, for example, glass or plastic. In some implementations, the base 150 also includes the electrical connections for power and data communication. For instance, in some cases, the base 150 includes a printed circuit board (PCB) designed to have one or more layers of electrical connections using any standard PCB computer aided design software and fabrication techniques (e.g., mask and chemical etching techniques). In certain implementations, the base 150 may be a substantially contiguous elongated board or frame.

The modular analytic system 100 also includes one or more sample processing modules 152, also called sample preparation modules. Each sample processing module 152 receives, contains, and stores one or more samples and may receive, contain, and store one or more reagents for performing assays of the sample(s). The sample processing module 152 can be in the form of a cartridge, chip, or any appropriate casing that is capable of receiving and storing the sample(s). Alternatively, the sample processing module can be a casing that is capable of receiving a separate cartridge (e.g., cartridge 106, which is received in slot 104 of FIG. 1) that, in turn, receives, contains, and stores one or more fluid samples and that may receive, contain, and store one or more reagents for performing assays of the sample(s). In the case the sample processing module 152 is capable of receiving a cartridge that stores the sample fluid/reagent, the sample processing module 152 can include connections that allow access to the fluid sample in the cartridge as well as connections that allow an actuation source to couple to the cartridge. Although the opening in the sample processing module for receiving the cartridge 106 is shown as a slot 104 in FIG. 1, the opening may be an appropriate aperture or space that is capable of receiving the cartridge.

In the example shown in FIG. 2, the sample processing module 152 includes separate receptacles 153 internal to the module, each of which is configured for a different use, such as storing the sample, storing the reagent, and storing/forwarding the sample after it has reacted with the reagent. Again, the receptacles 153 can be part of a separate cartridge that is received by the sample processing module 152. For instance, the cartridge can include a well plate with wells for storing the fluid sample, reagent, and forwarding the fluid sample and/or a mixture of the fluid sample and reagent. The sample processing module 152 can include internal fluidic channels (e.g., internal tubes) that connect the different receptacles so that the sample and reagent can be combined within the module 152 and transported from the module 152 to the fluidic network. In some implementations, the internal fluidic channels are formed as part of the sample processing module 152 and connect to a cartridge containing the receptacles when the cartridge is received by the sample processing module 152. The sample processing module 152 prepares the fluid sample to be tested (e.g., by combining the fluid sample with a reagent) and stores it in the store/forward receptacle until it is ready to be transferred from module 152 for further processing. The sample processing module 152 or a cartridge that is received by the sample processing module 152 can include multiple fluid sample receptacles, reagent receptacles, and store-forward receptacles, e.g., if the module 152 is used to perform multiple tests on the fluid sample.

The sample processing module 152 also is configured to securely mount to the base 150 while also being detachable from the base 150 for disposal, cleaning and re-use or to replace with another sample processing module. The sample processing modules can fluidly connect to one or more fluidic channels of the fluidic network through sealing areas formed on the base 150. Further details of the sample processing module and cartridges that may be received by the sample processing module can be found in U.S. Provisional Application 62/064,846, filed on Oct. 16, 2014, the subject matter of which is incorporated herein by reference in its entirety.

To transport the fluid samples (e.g., from the sample processing modules, through the fluidic network, to the analytical modules, and/or to waste channels), the modular analytic system 100 also can include a fluid actuation power source module 154. Similar to the preprocessing module 152, the fluid actuation power source module 154 can be configured to securely mount to the base 150 while also being detachable from the base 150. The fluid actuation power source module 154 can be temporarily coupled to the store/forward internal receptacle(s) of one or more of the sample processing module(s) 152 through standardized interface(s). For instance, the sample processing module(s) 152 can include an interface that includes one or more input actuation ports coupled to the store/forward receptacles, such that when the interface is coupled to the fluid actuation power source module 154, the pneumatic or hydraulic pressure output by the module 154 is delivered to the store/forward receptacle(s) of the sample processing module 152.

The fluid actuation power supply module 154 can be a device, such as a pneumatic or hydraulic pump, that provides a source of actuation (e.g., compressed gas) to force the fluid samples to move through the fluidic channels.

In the example shown in FIG. 2, the fluid actuation power supply module 154, when activated, applies pneumatic pressure through an actuation input port 149 of the store/forward receptacle, causing any sample and/or reagent contained within the receptacle to move from the sample processing module 152 to a fluidic channel through a fluidic output port 151 of the store/forward receptacle. The input port 149 and output port 151 can be part of standardized connector interfaces on the sample processing module 152. In some implementations, the input port 149 and output port 151 are fluidly coupled to the store/forward receptacle when the store/forward receptacle is a part of a cartridge received by the fluid sample processing module.

In some implementations, the modular analytic system 100 includes a single fluid actuation power source having an output (e.g., pneumatic or hydraulic) that is split into multiple different independent channels (e.g., one for each sample processing module) through a manifold. In other implementations, the modular analytic system 100 includes multiple independent fluid actuation power supplies, each of which is coupled to a separate sample processing module.

The modular analytical system 100 also includes one or more analytical modules 156. Similar to the sample preprocessing modules 152, the analytical module(s) 156 are supported by the base 150 and are configured to securely mount to the base 150 while also being detachable from the base 150 for cleaning and re-use or to replace with another analytical processing module. In some cases, the analytical module(s) 156 may be disposable. The analytical module(s) 156 can be in the form of a cartridge, chip, or any appropriate casing that is capable of receiving and storing the sample(s). The analytical module(s) 156 include components that are configured to analyze the fluids transported from the sample processing module(s). For instance, the analytical module(s) 156 can include hardware components such as sensors, electronic processors, and memory, among other electronic components, for performing measurements of fluids, for generating and processing measurement data resulting from the measurements, and for transmitting the signals to a central processing unit for further analysis.

In the example shown in FIG. 2, the analytical module 156 includes a signal source 157 (e.g., a light source such as a light emitting diode or laser, a voltage source, an electric current source, or other signal source) configured to generate a signal for interacting with the fluid, a detector 159 configured and arranged to detect the signal after the signal has interacted with the fluid and to generate measurement data, and module electronics 161 configured and arranged to receive the measurement data and perform pre-processing on the measurement data (e.g., perform noise reduction on the measurement data, amplify the measurement data, or perform other signal conditioning). The analytical module 156 also can include a measurement receptacle 163 for holding the fluid received from a sample processing module or from another analytical module. The measurement receptacle 163 can include an input port 165 for receiving a fluid from a fluidic channel through a seal on the base 150 or from tubing coupled to the base 150. The measurement receptacle 163 also can include a fluid output port 167 for coupling to another fluidic channel so that the fluid can be transferred from the analytical module 156 after measurement (e.g., to a waste chamber or to another analytical module). Further details on fluid sample analytical modules can be found in PCT Patent Application Publication No. WO2014078785, filed Nov. 18, 2013 and entitled "SYSTEM AND METHOD FOR INTEGRATED MULTIPLEXED PHOTOMETRY MODULE," and PCT Application No. PCT/US2014/062426, filed on Oct. 27, 2014 and entitled "MODULAR INSTRUMENTATION FOR ANALYZING BIOLOGICAL FLUIDS." The subject matter of each of those applications is incorporated herein by reference in its entirety.

The modular analytical system 100 also can include a central processing unit (CPU) 158 that is supported by the base 150. The CPU 158 can be electronically coupled to one or more of the different modular components of the system 100 through wiring and electronic interfaces formed in or on the base 150. The CPU 158 includes an electronic processor and may have other hardware components (e.g., memory, switches, or other active and passive electrical components) for generating control signals and for receiving and analyzing measurement signals from the analytical modules. The CPU 158 also can include a communication port for electronically receiving external input signals (e.g., from another computer) and for transmitting output signals (e.g., measurement data) to a display or other computer.

The modular analytical system 100 also can include a waste container (not shown in FIG. 2) that is supported by the base 150 and is configured to securely mount to the base 150 while also being detachable from the base 150 for cleaning and re-use or for being replaced with another waste container. The waste container is coupled to the fluidic channels downstream from the one or more analytical modules 156 and collects waste fluids that have passed through the analytical modules after analysis.

Figure 3:
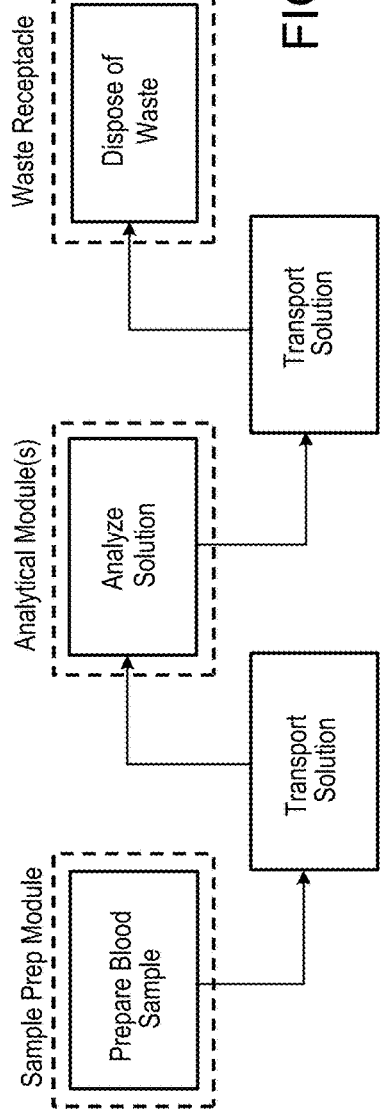
FIG. 3 is a schematic that illustrates an example of a general process covered by a modular analytic system.

FIG. 3 is a schematic that illustrates an example of a general process covered by the modular analytic system 100. First, a fluid sample (e.g., a biological fluid sample such as blood) is received in a sample preparation module (such as module 152 in FIG. 2), where the fluid sample may be stored, separated into aliquots, mixed, and/or incubated with a reagent. For performing the sample preparation actions (e.g., mixing, incubation, separation), the CPU can send control signals to the sample preparation module to instruct the module to perform the desired actions. The fluid sample may be manually loaded into the sample preparation module using, for example, pipetting. When loading the fluid sample, the module can be positioned on and attached to the base 150 or located separate from the base 150. If separate, the sample preparation module can be attached to the base 150 after loading such that the fluidic output(s) from the module fluidly couple to one or more fluidic channels of the fluidic network.

After loading the fluid sample and performing any applicable sample preparation (e.g., obtaining aliquots, mixing and incubation), the fluid actuation power supply (e.g., pneumatic power supply 154) may be activated to transport the prepared fluid sample from the preparation module (e.g., from the store/forward receptacle) through the attached fluidic channels to the appropriate analytical module, where the prepared fluid sample is analyzed. In some implementations, certain sample preparation steps, such as mixing and incubation are performed on a second separate sample preparation module that receives the fluid sample from the first sample preparation module. After performing the analysis, the pneumatic supply may again be activated to transport the fluid sample from the analytical module to the waste container through the fluidic channels. The activation of the fluid actuation power supply, sample preparation modules, and analytical modules can be controlled by the CPU.

Figure 4:
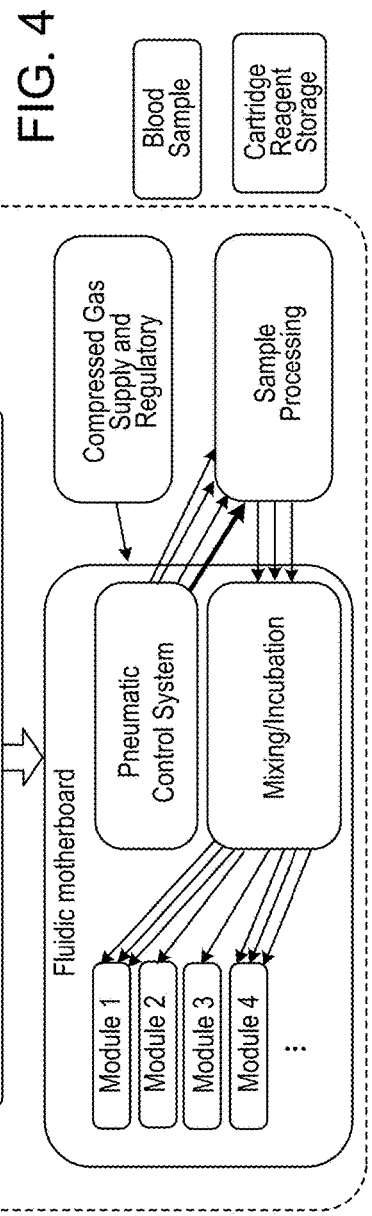
FIG. 4 is a schematic illustrating the operational connectivity of an example of a modular analytic system.

FIG. 4 is a block diagram illustrating a schematic setup of the modular analytic system and the interaction of the various components. In the system, a blood sample (which could be another type of sample or samples as noted herein) is introduced into a sample preparation module (e.g., a cartridge) that may also be used to store one or more reagents. This cartridge can be placed in communication with the fluid network and modules after the sample or samples are processed. The processed samples may be provided to a mixing/incubation module on a fluidic network board before being transported to one or more analytic modules which are also disposed on the fluidic network and are in communication with the mixing/incubation module. As explained above, to transport the fluid sample between the various stages and modules, a pneumatic control system and/or a hydraulic control system may be used. If, for example, a pneumatic control system is used, then this system may receive compressed gas from a compressed gas supply and regulator. The various stages and modules may be connected to electronics such as a controller for controlling and communicating with the various modules and for routing various signals. In some instances, these electronics may be in communication with a computer that includes software and a graphical user interface (GUI) for controlling operation of the system.

Figure 5:
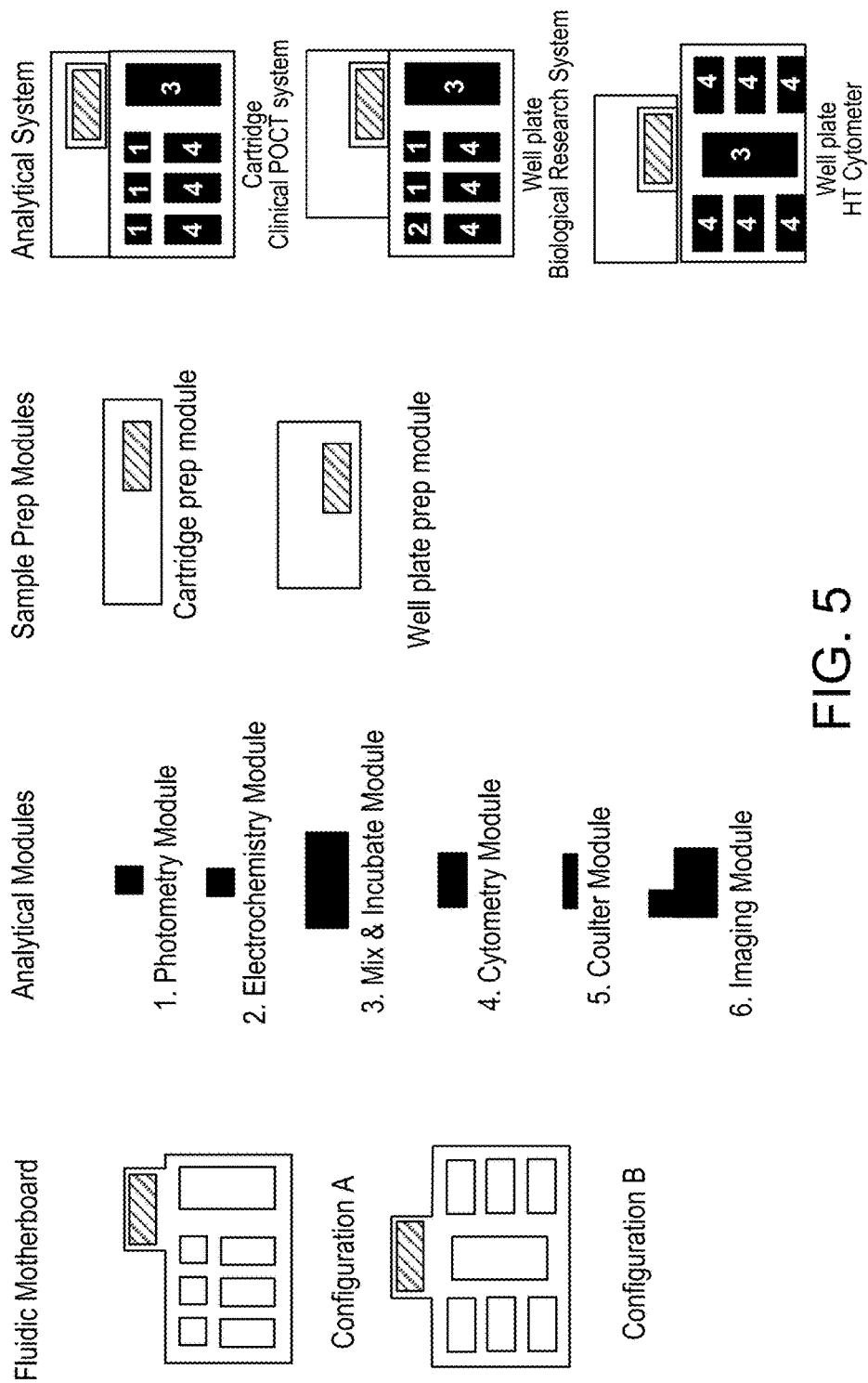
FIG. 5 is a high-level schematic overview that illustrates how a number of components can be arranged to create different examples of modular analytic systems according to various aspects described herein. This figure shows alternative configurations for the fluidic network or motherboards, lists a number of analytic modules that may be selectively connected to the network, some options for sample preparation modules, and some examples of combined analytic systems constructed from these components.

Now with additional reference to FIG. 5, some of the various components that could be used to construct the modular analytic system are illustrated, as well as systems that could be constructed using these components.

In the first column of FIG. 5, two different configurations of fluidic networks or motherboards are illustrated: Configuration A and Configuration B. In both instances, there are various sets of connectors on the fluidic networks (indicated by the internal rectangles) that may be adapted for configuration to either a sample preparation system/module or an analytic module. It is noted that the two illustrated networks are only illustrative and are not the only two configurations that the fluidic networks may have.

In the second column of FIG. 5, various analytical modules are illustrated that may be selectively connected to the fluidic networks. These include (1) a photometry module, (2) an electrochemistry module, (3) a mix and incubate module, (4) a cytometry module, (5) a Coulter module, and (6) an imaging module. The illustrated analytic modules do not constitute the only modules that can be used and are only representative of some of the envisioned modules. For the purposes of distinguishing the modules from one another in the illustration, they are each given a different size and/or shape and, in the fourth analytical system column, are provided with numbers that correlate to their identification in the second column. It is contemplated that different types of modules do not necessarily need to have a different size and shape and, in some instances, may actually have similar sizes and shapes so that connectors (described in greater detail below) may be standardized to match the matching or corresponding connectors on the fluidic network for attachment. However, it is also contemplated that the shapes and sizes might intentionally be made different to help an end user distinguish between the various modules and/or to help indicate to the user that a particular module is connectable to a particular set of connectors on the fluidic network.

In the third column, two examples of sample preparation modules or systems are illustrated including a cartridge preparation module and a well plate preparation module. A cartridge preparation module may be more appropriate for the use in a clinical environment, whereas a well plate preparation module may be more appropriate for use in a research environment. Again, types of sample preparation modules may be used other than those illustrated and it is contemplated that the system could also receive one or more sample preparation modules at the same time (even in a single analytic system) or be adapted to receive more than one type of sample preparation module.

In the fourth column, some exemplary analytic systems are illustrated that have been constructed using the components from the first three columns. As a first example, a cartridge clinical point of care testing system is illustrated as being buildable from configuration A of the fluidic network, three photometry modules, three cytometry modules, a mix and incubate module, and a cartridge preparation module. As a second example, a well plate biological research system is buildable from configuration A of the network, an electrochemistry module, two photometry modules, three cytometry modules, a mix and incubate module, and a well plate preparation module. As a third example, a well plate high throughput (HT) cytometer is built using configuration B of the network, six cytometry modules, a mix and incubate module, and a well plate preparation module. Again, these three examples are for illustrative purposes only, and it is contemplated that various other types of analytical systems could be built using the modular components that are disclosed or other modules and/or fluidic network configurations.

FIGS. 6A through 6D illustrate an example of an assembly 200 of a fluidic network 202 and various modules, outside of any case or housing in which the system may be received. This particular assembly 200 includes the fluidic network 202 that is similar to the configuration A network illustrated in FIG. 5. This network 202 has a mix and incubate module 204, three photometry modules 206, 208, and 210, and three cytometry modules 212, 214, and 216 attached thereto. It should be noted that these various modules 204-216 may be selectively connected to the fluid network 202 in a plug-and-play type manner such that the modules 204-216 may be readily added or removed from the network 202 to promote easy construction and maintenance of the system 200.

The plug-and-play type connections may be between the modules 204-216 and the network 202 and include an intermediate connection assembly including tubes, gaskets and so forth as will be described in greater detail below. Further, in the form illustrated, the plug-and-play connections are primarily fluidic in nature (i.e., placing the various channels in the modules in fluid communication with channels or openings formed in the fluidic network). Separate electrical or data connections are available on the outside of the modules for connection to a controller or controllers for transmitting (i.e., sending or receiving) data or signals from the modules and/or providing power to the modules. In the form illustrated, these electrical connectors are shown on the lateral sides of some of the modules 204-216 (e.g., see the connectors on the front side of the modules 206-210 in FIG. 6B). However, it is contemplated that attachment of the modules to the network could also include connections of an electrical type to permit transmission of electrical data, signal, or power, for example in addition to these fluidic connections.

Figure 6A:
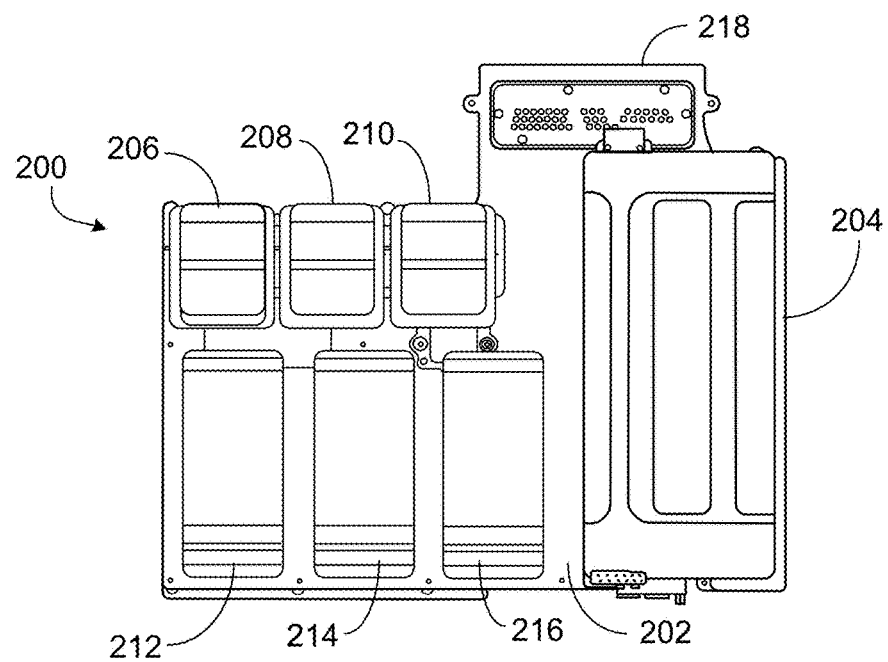
FIG. 6A is a top view of a fluidic network with various modular detectors and a mixing module attached thereto.
Figure 6B:
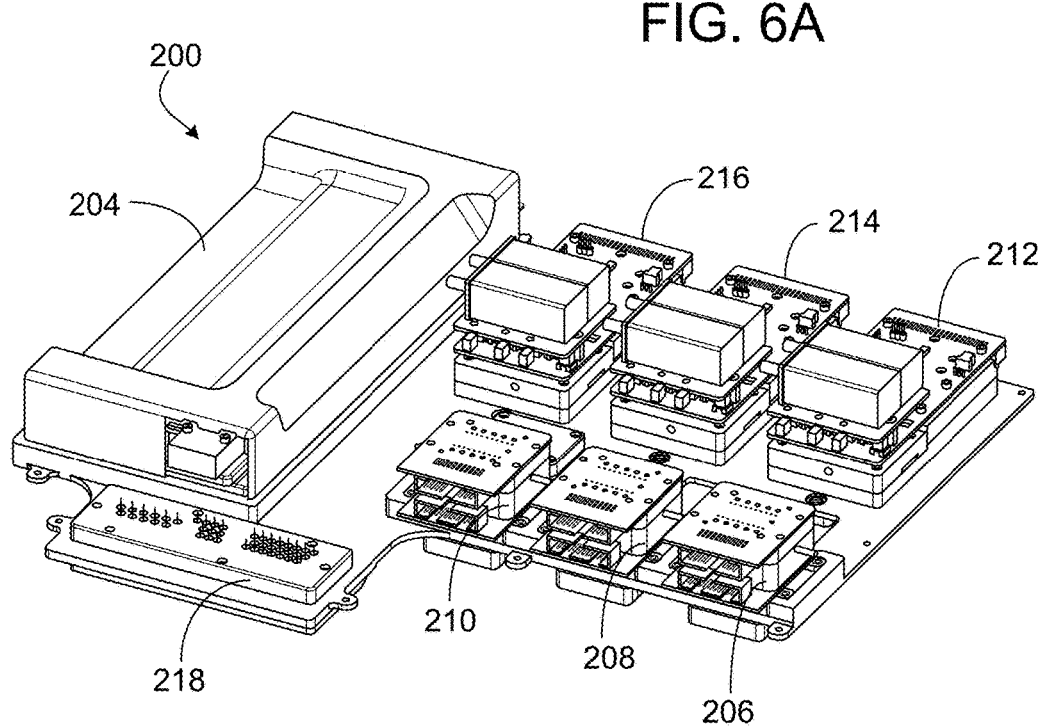
FIG. 6B is a top side perspective view of the fluidic network with various modular detectors and the mixing module attached thereto from FIG. 6A (albeit with the housing or covers from some of the modules removed to reveal the interior parts).
Figure 6C:
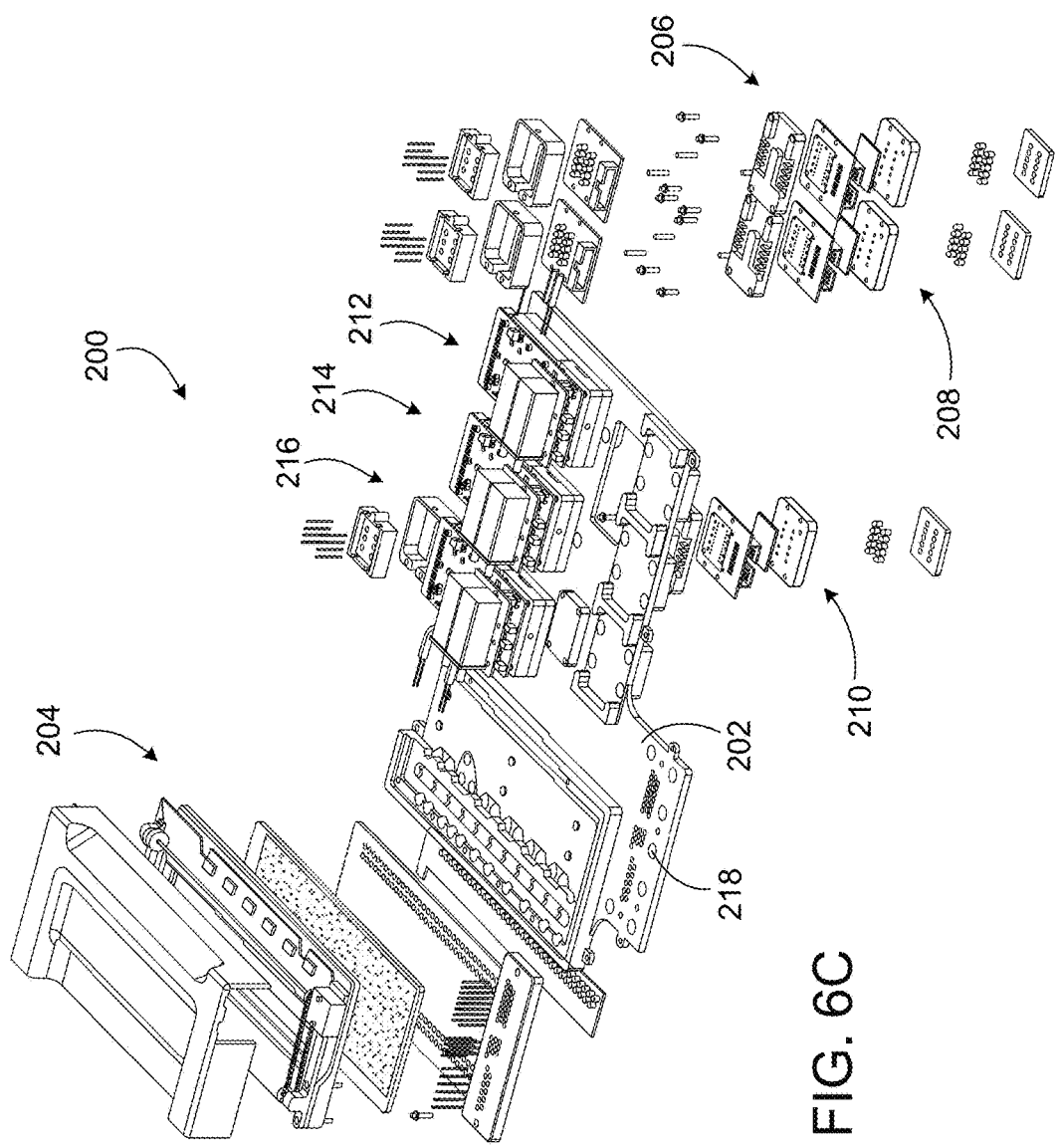
FIG. 6C is a top side partially exploded perspective view of the assembly shown in FIG. 6B revealing some of the various components in the various modules.
Figure 6D:
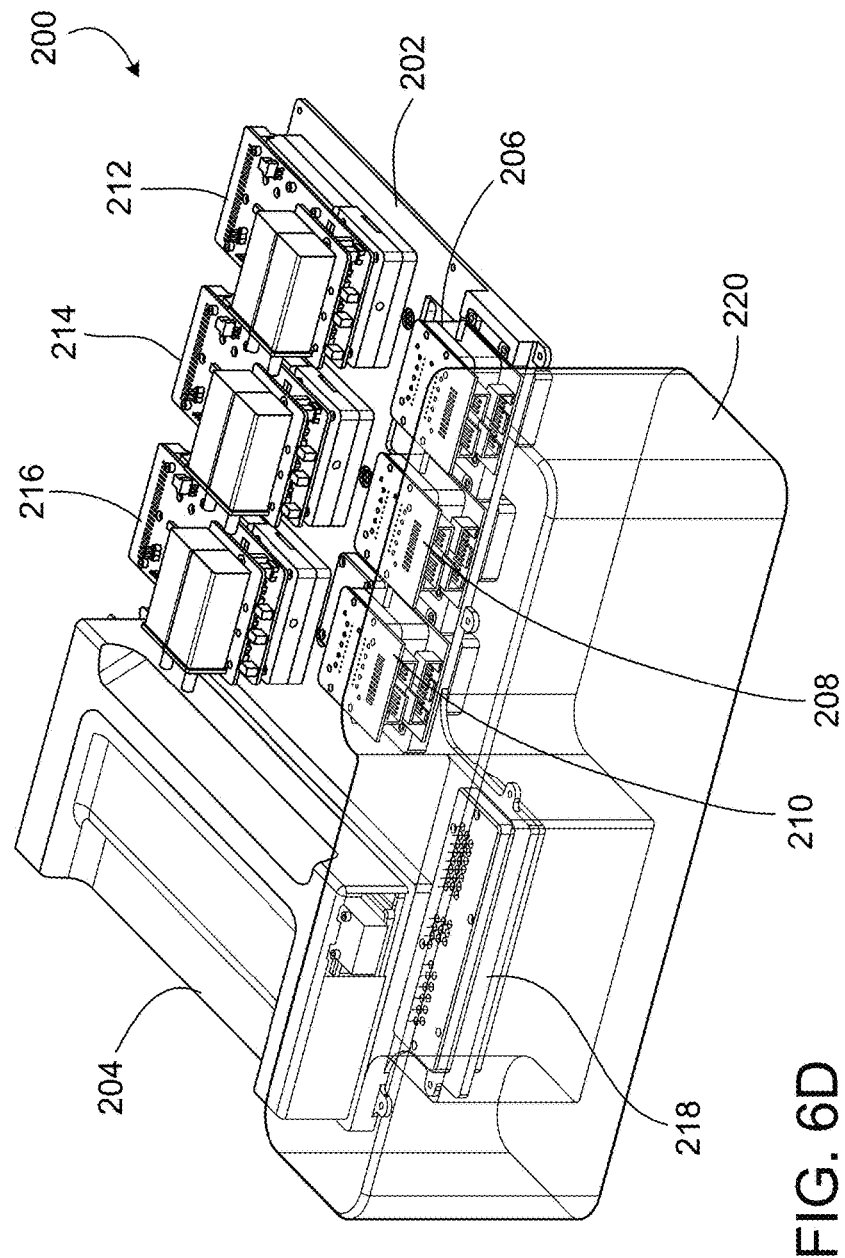
FIG. 6D illustrates the fluidic network and modules of FIG. 6B in which a sample preparation system is schematically illustrated as being connected to the network to provide sample (s) and/or reagent(s).

The fluidic network 202 also includes a set of connectors 218 for connection to a sample preparation system 220 or module. With reference to FIG. 6D, the assembly of FIGS. 6A through 6C is shown with the sample preparation system 220 or module attached to the network 202 at this set of connectors 218 which is adapted to place the fluidic channels of the fluid network 202 in fluid communication with channels or reservoirs in a sample preparation system 220, when the sample preparation system 220 is attached. The attachment of the sample preparation system 220 to the network is abstractly illustrated in FIG. 6D. The sample preparation system 220 is attached to provide one or more test samples (e.g., blood, urine, etc.) and/or one or more reagents to the fluidic network 202 via the set of connectors 218. The fluid can be drawn out of the sample preparation system 220 or module using a hydraulic or pneumatic module attached to the network 202 and in communication with the fluidic channels in the network 202 or can be transported into the fluidic system using some transport mechanism that is integrated with the sample preparation system 220 or module.

The sample preparation system 220 or module can take a number of forms. It is contemplated that it could be a cartridge (as may be common in a clinical environment), a pipetting/well plate configuration (as may be common in a research environment), or some other type of sample preparation system.

Figure 7A:
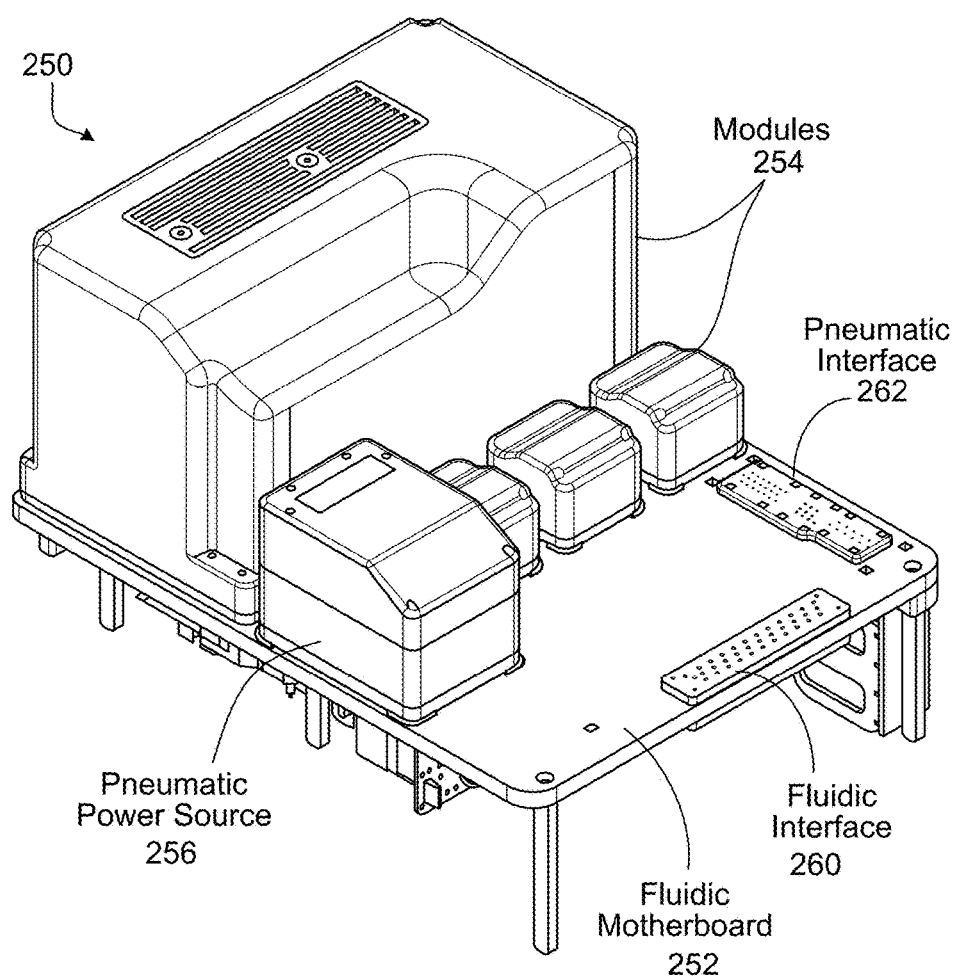
FIGS. 7A-7E are schematics that illustrate various views of a modular analytic system.
Figure 7B:
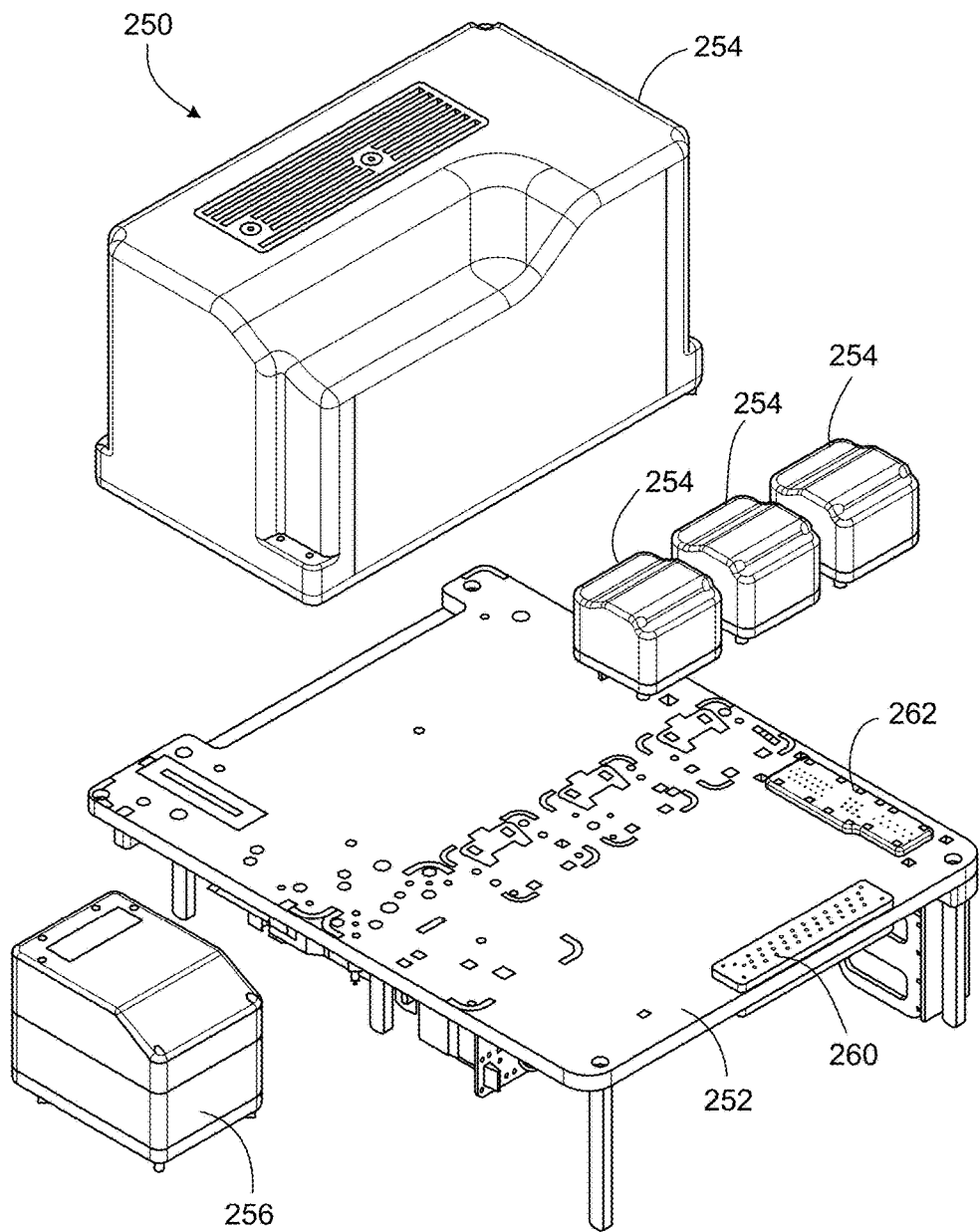
Figure 7C:
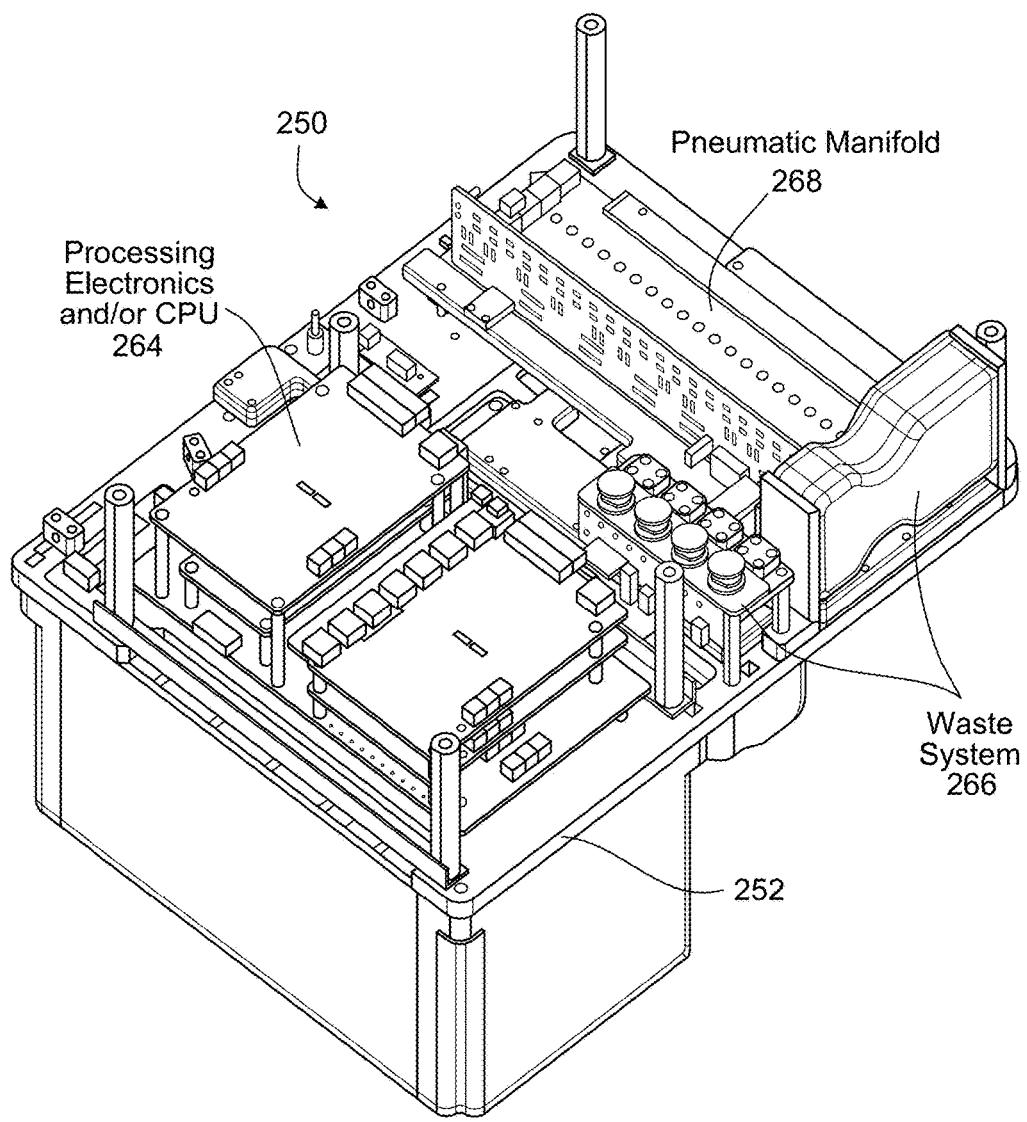
Figure 7D:
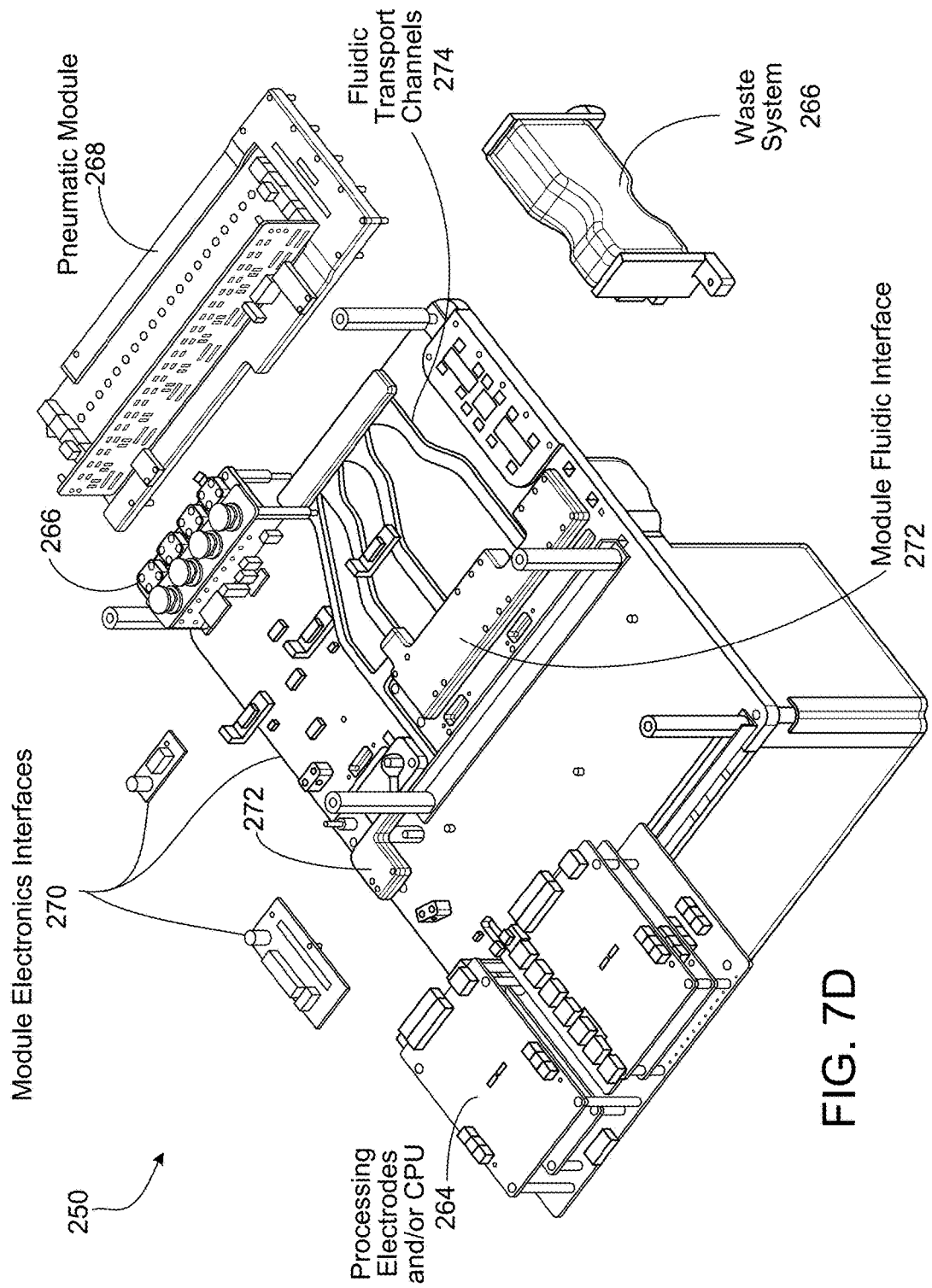
Figure 7E:
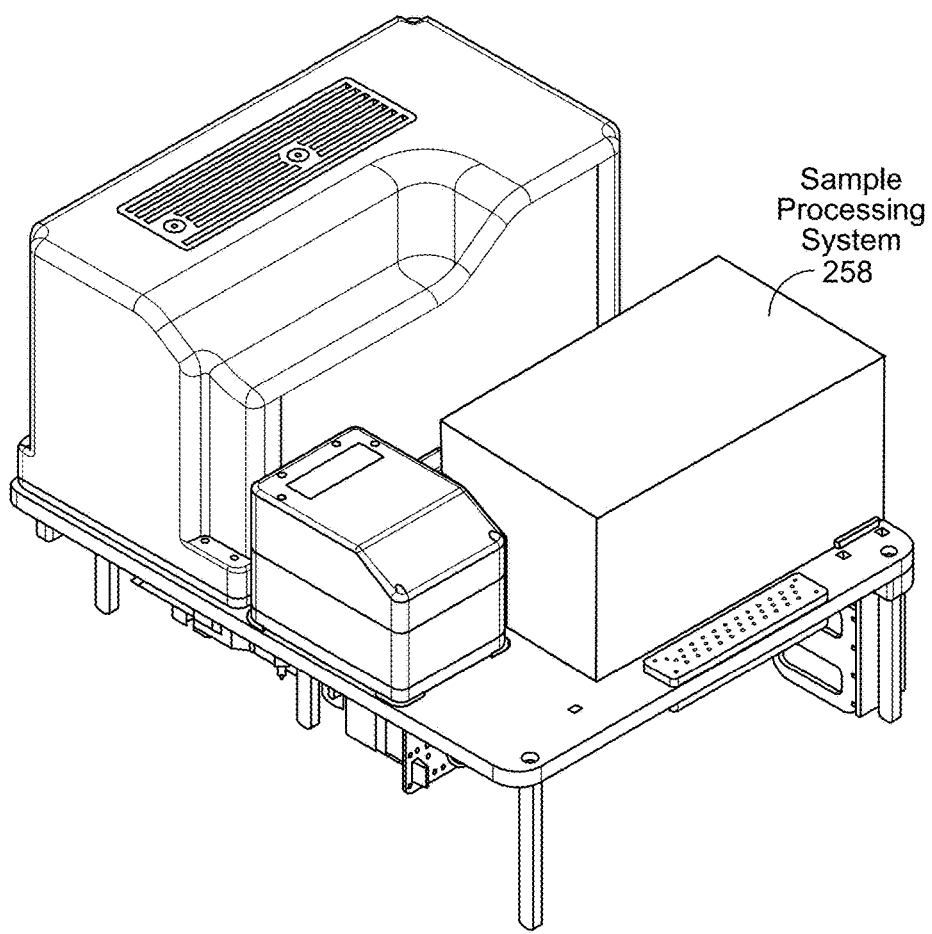

FIGS. 7A-7D illustrate an alternate example of a modular analytic system 250. As shown in FIG. 7A, the system 250 includes a base/fluidic motherboard 252 that supports multiple detachable modules 254 and a detachable pneumatic power source 256. The detachable modules 254 include one or more sample processing modules and one or more analytical modules. For instance, the detachable modules 254 can include modules for mixing and/or incubating fluid samples with reagents, modules for performing assays, modules for performing photometry, and/or modules for performing cytometry, among other types of modules. As noted, the pneumatic power source 256 serves as the power source for actuating fluids amongst the various sample handling modules. The board 252 also supports the fluidic network for routing the prepared sample from the detachable modules to one or more other detachable modules or to a waste container. Referring to FIG. 7E, the board 252 also can include a detachable sample preparation module 258. When the sample preparation module 258 is attached to the board 252, channels or wells contained within the module 258 fluidly couple to a fluidic interface 260 (see FIG. 7A). In addition, the module 258 also is coupled to the pneumatic power supply through a pneumatic interface 262 (see FIG. 7A).

When the sample preparation module 258 is attached, the module 258 is able to provide one or more test samples (e.g., blood, urine, etc.) and/or one or more reagents to the fluidic network through the fluidic interface 260. The fluid can be drawn out of the sample preparation module 258 using the pneumatic power supply 256 that is in communication with the module 258 through the pneumatic interface 262. FIG. 7B is a schematic that shows a perspective view of the modular analytic system 250 with the modules 254 and pneumatic power supply 256 detached from the board 252. FIG. 7C is a schematic that illustrates a reverse side of the board 252. As shown in FIG. 7C, the board 252 also supports processing electronics 264, including a CPU. The processing electronics 264 can be coupled to the various modules through electrical connections to permit transmission of electrical data signals, control signals, and/or power signals. The board 252 also supports a detachable waste container 266. The waste container is coupled to the fluidic channels downstream from the one or more modules 254 and collects waste fluids that have passed through the analytical modules after analysis. Additionally, the board 252 can include a manifold 268 (e.g., a pneumatic manifold). The manifold 268 is coupled to the pneumatic power supply 256 and enables the air pressure provided by the power supply 256 to be divided into multiple separate pneumatic channels, where each pneumatic channel can then be used to actuate fluid samples from different modules. FIG. 7D is a schematic illustrating an exploded view of the reverse side of the board 252, and showing the module electronic interfaces 270 (for coupling electronic signals to and from the processing electronics 264), the backside of the module fluidic interfaces 272 for fluidly coupling the fluidic channels to the modules, and the backside of the fluidic transport channels 274.

Figure 7F:
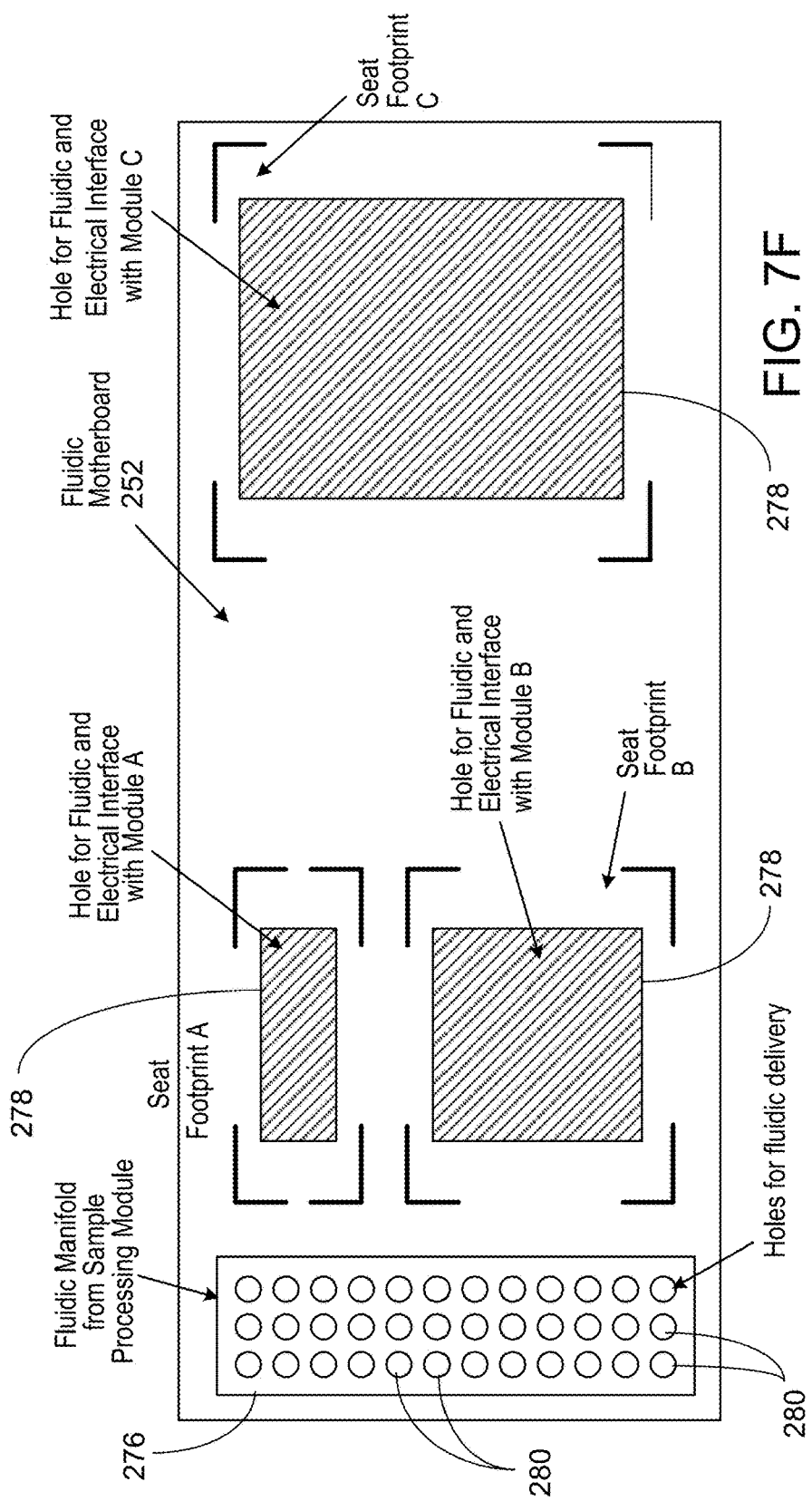
FIGS. 7F-7G are schematics that illustrate two different possible fluidic connection configurations to a fluidic motherboard.
Figure 7G:
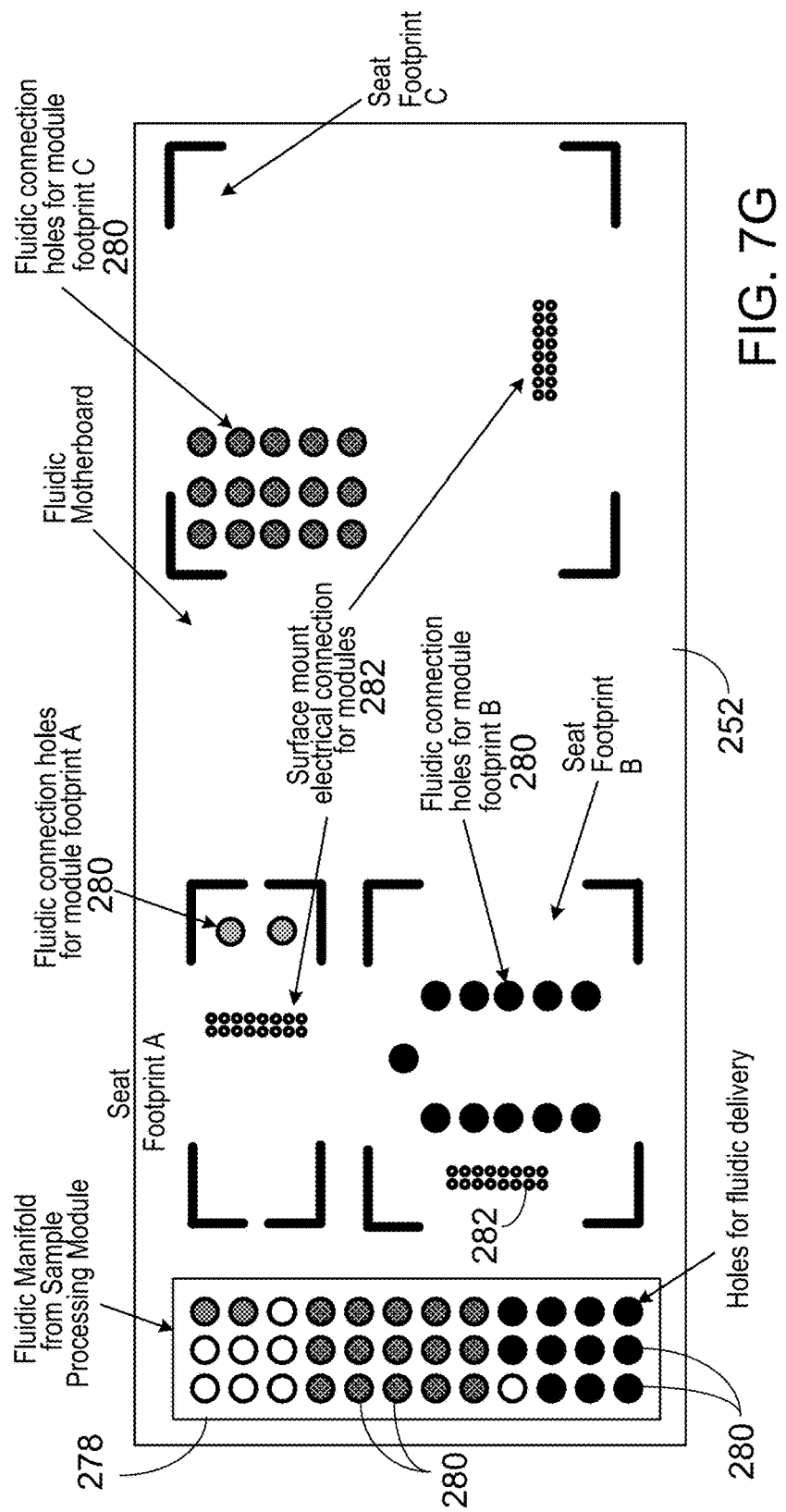

The fluidic connections that couple the pneumatic power supply, the modules and the waste container can have various configurations. FIGS. 7F and 7G are schematics that illustrate two different possible fluidic connection configurations to a fluidic motherboard. In both configurations, the fluidic motherboard contains a fluidic manifold that delivers prepared sample from the sample processing module through one of multiple access ports.

The configuration shown in FIG. 7F is referred to herein as "completely variable." In this configuration, the fluidic motherboard 252 contains a set of module seats (three example footprints are shown) that can accommodate a module of a particular sized footprint. Within each module seat, there is a large access hole 278 in the fluidic motherboard 252 through which the module can be fluidly connected to the fluidic manifold 276 that contains multiple fluidic access holes 278. This connection can be made by fluidic channels that interface with the fluidic access holes 278 and the module. The fluidic channels can be in the form of tubes for carrying the fluid samples. The ends of the tubes can be coupled together in a coupler or "fluidic header," that attaches to the manifold or the module. Thus, for a particular module, one fluidic header connects to the fluidic manifold and the other connects directly to the module itself. The tubes corresponding to the fluidic channels can be held together in a tube ribbon/bundle or free standing tubes.

Through the large access hole 278 in the module seat, the module is also connected electrically to the remainder of the analyzer electronics. With this configuration, modules can be replaced with the only constraint being that they have to fit into one of the available footprints. The number and location of fluidic and electrical connections to each module are completely variable and so, the system can be reconfigured such that any module can access any port in the fluidic manifold.

The configuration shown in FIG. 7G is referred to as "Semi Variable." In this configuration, the fluidic motherboard 252 contains a set of module seats that have predefined fluidic access holes 280 and electrical connection sites 282. In this case, the ports in the fluidic manifold are "hardwired" to particular fluidic access hole locations on the fluidic motherboard or to a particular module seat. For instance, the ports can be coupled to the access holes or modules seats through defined fluidic channels formed within the board itself. Alternatively, the fluidic channels can include tubes arranged in a ribbon/bundle or free standing tubes. For the modules to properly attach to the board 252, the modules must have a spatial footprint that conforms to the seat dimensions and each module's fluidic and electrical connections must be located at pre-determined locations corresponding to the access holes 280 and electrical connection sites 282 when the modules are positioned on the board 252. Although not shown, the fluidic mother board in either the completely variable or the semi variable configuration can include openings (e.g., grooves) or protrusions that are configured to mate with protrusions or openings, respectively, on the modules, so that the modules may be removably attached to the board surface.

Figure 8:
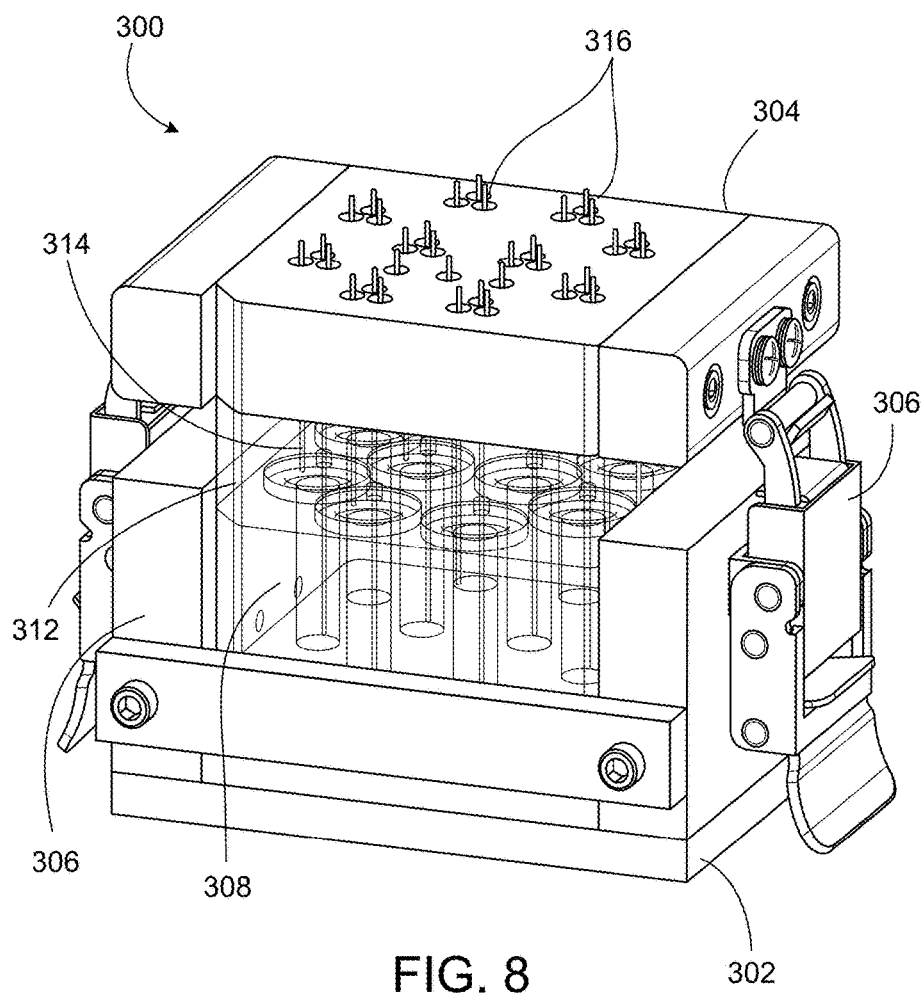
FIG. 8 is a three-dimensional schematic that illustrates an example of a sample preparation system in the form of a sample handler.

An example of a sample preparation system 300 is illustrated in FIG. 8. In this example, sample preparation system 300 includes a housing or frame with a lower half 302 and an upper half 304, which are fastenable together via side attachment latches 306. The lower half 302 and the upper half 304 are arranged between a sample tray 308 and an intermediate member 312. The sample tray 308 is receivable in the lower half 302 (i.e., may be seated in the lower half 302) and includes a number of wells 310 for receipt of samples, sample vials or containers for holding samples, reagents, or vials or containers for holding reagents. The intermediate member 312 is placed between the sample tray 308 and the upper half 304 and includes a number of channels 314. These channels 314 place the wells 310 (or the sample or reagent holders received therein) in communication with channels or conduits formed in the upper half 304 of the housing. The exposed connections 316 on the top of the upper half 304 of the housing of the sample preparation system 300 may then be adapted for connection to a fluidic network of the modular analytic system (via the channels or conduits, for example). There are multiple channels for each well illustrated so as to create a circuit that accommodates circulation and pumping of fluids from the wells into the system and vise-versa.

Figure 9A:
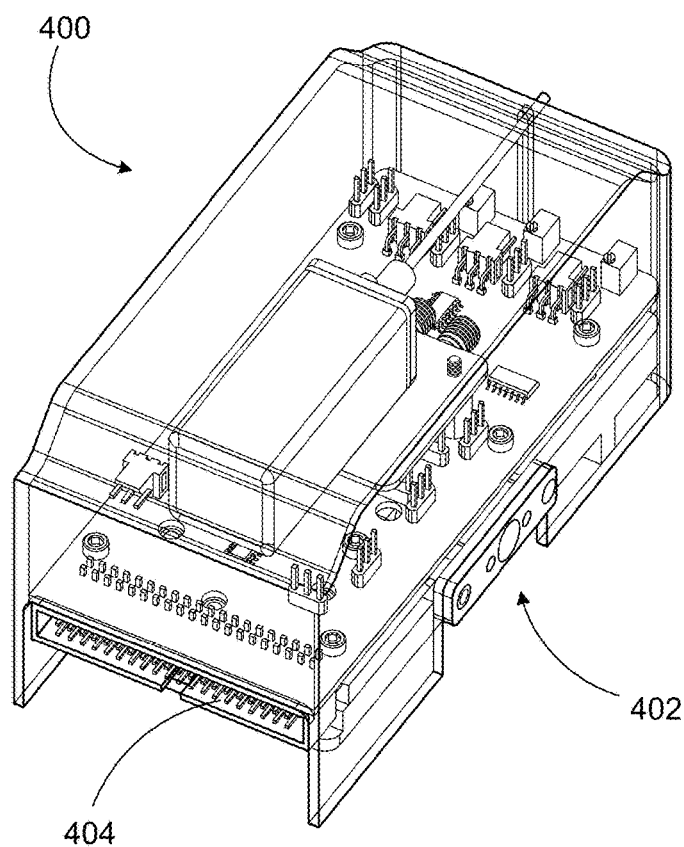
FIG. 9A illustrates an example of an integrated cytometer module (ICM).
Figure 9B:
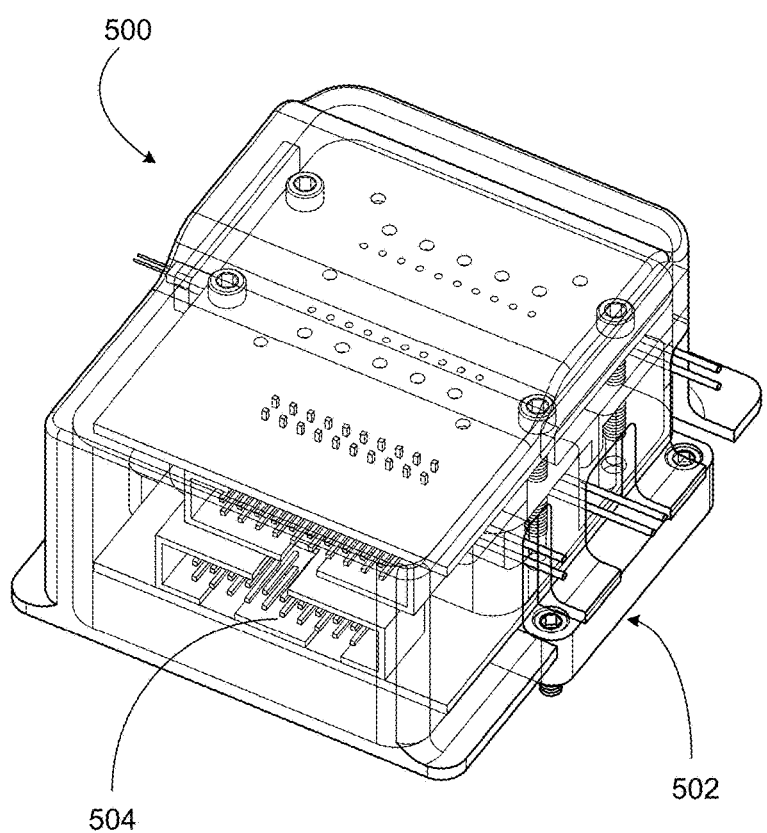
FIG. 9B illustrates an example of an integrated photometry module (IPM).
Figure 9C:
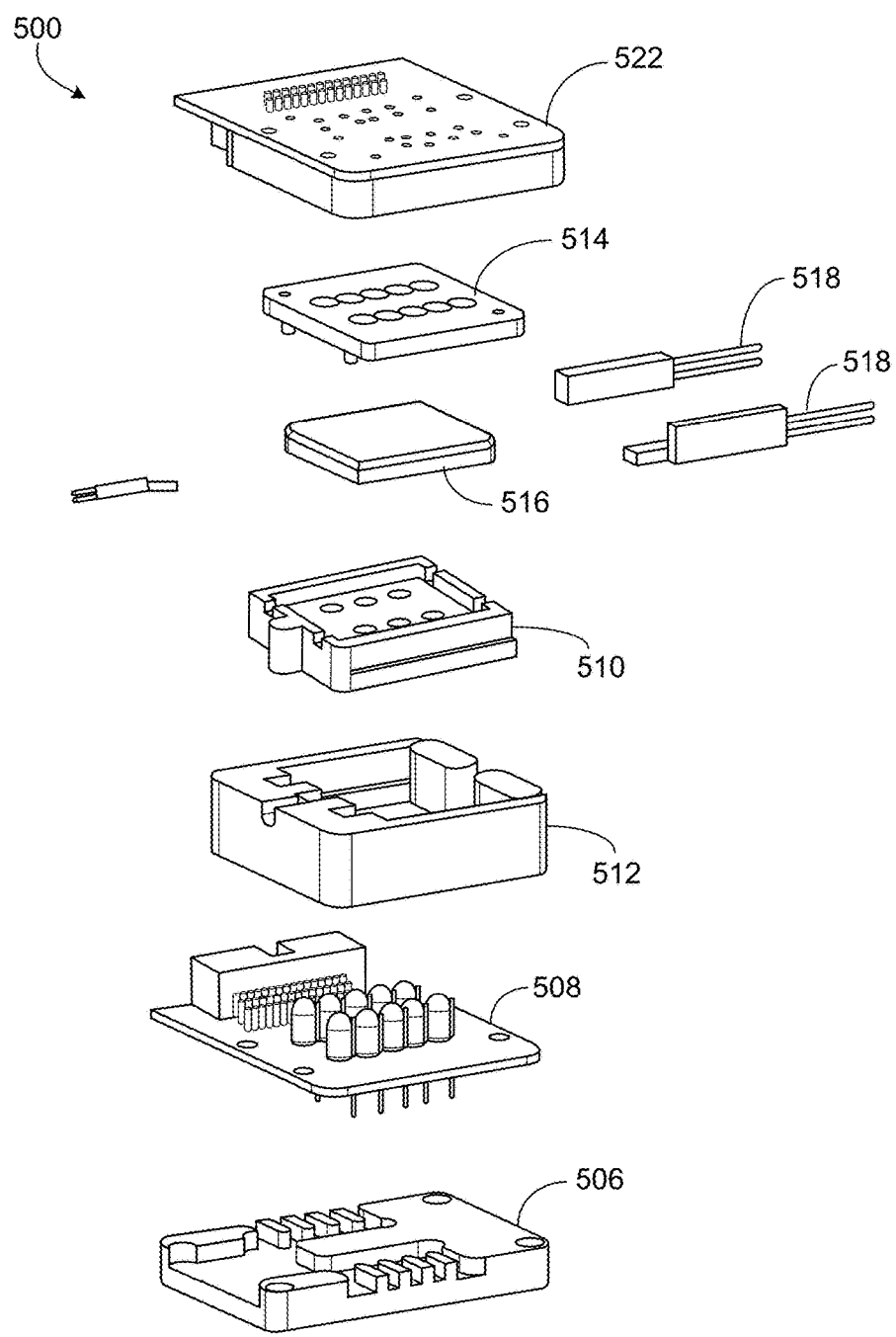
FIG. 9C is an exploded view of the integrated photometry module in FIG. 9B.

The sample preparation system 300 illustrated in FIG. 8 is only one example of a sample preparation system and there may certainly be mechanical variations to this system or other types of sample preparation systems utilized in the modular analytic system. Turning now to FIGS. 9A-9C, examples of two analytical modules are shown apart and detached from the fluidic network.

In FIG. 9A, an integrated cytometry module 400 is illustrated for performing flow cytometry which includes the components to analyze particles in a biological sample. For example, a fluid sample processed by the integrated cytometry module 400 will identify particles or constituents of a sample having a particular specified quality. The various components of the integrated cytometry module 400 may include a laser and light and/or color detectors for transmitting light through particles or cells in the fluid sample being tested and for receiving the forward scatter or emitted light from the florochromes of the particles or cells, a means (typically a flow chamber) for ensuring that the particles or cells of the biological sample are aligned as they flow through the area between the laser and the light detector, any filters appropriate to direct the emitted light to the appropriate color detector, and the associated electronics used to operate the module and/or assist in detection or quantification, amplification, and so on of the detected light signals. While the specific details of the components of the module 400 are not described in great detail, it is observed that the module 400 is adapted for connection to a fluidic network on its bottom side 402 (usually using tubes and one or more gaskets) so as to receive the fluid sample for testing. Further, there is an electrical connector 404 on the front side of the module 400 that may receive a plug for connection to a controller or other computer system that can provide a data connection as well as be used to supply power to the module 400. The particular integrated cytometry module 400 illustrated has two forward scatter, one side scatter, and one fluorescent channel for performing complete blood counts, cellular immunophenotyping and immunoassays. In terms of size, the integrated cytometry module 400 can have a very small package size and in one embodiment may be 6.5 inches by 2.5 inches by 3.5 inches.

In FIG. 9B, an integrated photometry module 500 is illustrated. Each photometry module 500 may contain 10 independent cuvettes giving the overall system the capability of performing 15 chemical assays in parallel. The remaining 15 cuvettes may run a standard blank for quality control. The 10 channel multiplex photometer can have wavelengths ranging from 400-800 nanometers to cover the full spectrum of clinical chemistry analytes. As with the ICM 400, the integrated photometry module 500 has a set of fluid connectors on its bottom side 502 and a set of electrical connectors 504 on its front side for data and/or power connection. In the illustrated form, the integrated photometry module 500 may have dimensions of approximately 3.5 inches by 2.5 inches by 3 inches.

Looking at FIG. 9C, the integrated photometry module 500 of FIG. 9B is exploded to show the various internal components of the module 500. The module includes a coupling manifold 506, an LED board 508, a plastic housing 510, aluminum heat sinks 512 and 514, a chip 516 with fluid channels for the testing sample interposed between the heat sinks 512 and 514, Peltier heaters 518, a resistance temperature detector (RTD) 520, and a detector board 522. In operation, the fluid sample flows through the chip 516 and light produced from the LED board 508 is transmitted through the fluid sample in the chip 516 (and apertures in the heat sinks 512 and 514 surrounding the chip 516) and is detected by the detector board 522.

Again, the modules 400 and 500 are illustrative of modules that may be connected to the fluidic network in a plug-and-play type fashion according to one aspect of the invention. Of course, the types of modules should not be limited to either these types of modules nor to the specific types or construction of the modules illustrated.

Figure 10A:
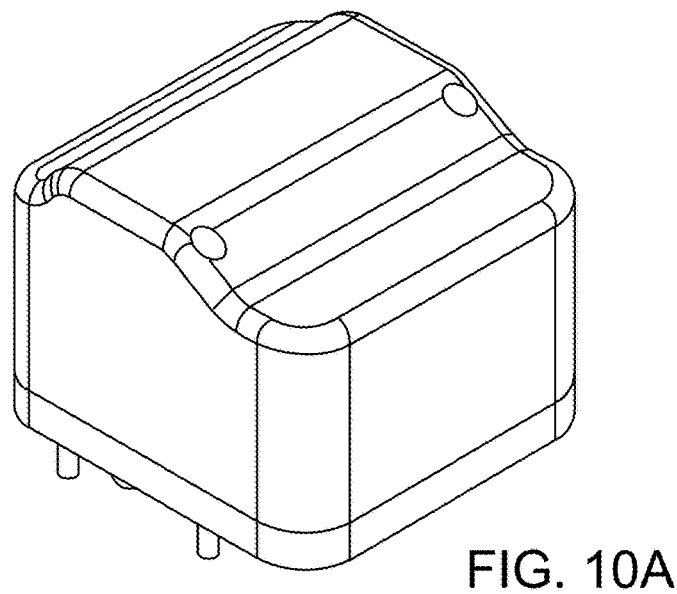
FIGS. 10A-10B are schematics that illustrate an example of an analytical module that fits into a module seat of a fluidic motherboard.
Figure 10B:
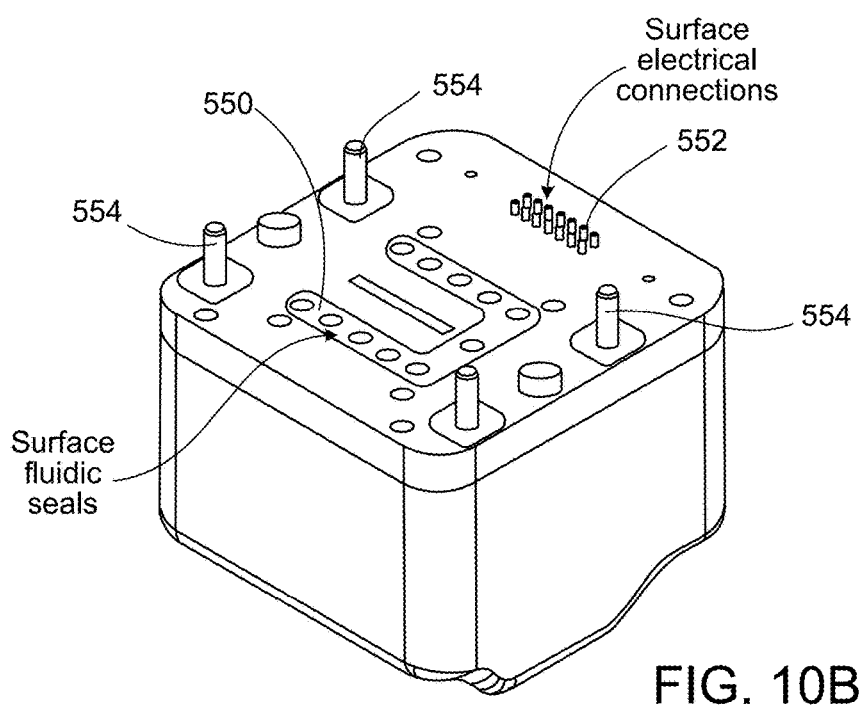

FIGS. 10A and 10B are schematics illustrating another example of a detachable analytical module that fits into a module seat of a fluidic motherboard, such as the seats shown in FIG. 7G. FIG. 10A is a perspective view of the top surface of the module whereas FIG. 10B is a perspective view of the bottom surface of the module. As shown in FIG. 10B, the surface fluidic seals 550 (e.g., gaskets or O-rings) and surface electrical connections 552 are illustrated as well. The fluidic seals 550 and surface electrical connections 552 can be removably attached to corresponding interface connectors formed on the fluidic motherboard.

In addition, the detachable analytical module includes protrusions 554 that fit securely into and mate with corresponding holes or openings in the fluidic motherboard. The protrusions 554 can be posts, ridges, flanges, bumps or other mechanisms that allow the module to be properly positioned and fixed in place on the fluidic motherboard. In some instances, the friction created by the protrusions helps secure the module to the board. This is also known as an interference fit, frictional fit, or press fit. Though protrusions are shown on the bottom surface of the module in FIG. 10B, other mechanisms allowing the module to be detachably secured to the board also can be used. For example, instead of protrusions, the bottom surface of the module may contain grooves or other openings configured to receive and mate with corresponding protrusions formed on the surface of the fluidic motherboard, such that the protrusions and grooves form an interference fit/frictional fit/press fit. Alternatively, the module and board may include any suitable latching mechanism that can be secured to hold the module in place on the board and unsecure to allow the module to be removed from the board. In some implementations, the module is secured to the board solely through the electrical and fluidic connections. Modules other than the analytical modules (e.g., the sample processing modules, the fluidic actuation modules, the waste container, and the CPU) also can include any of the foregoing mechanisms for detachably securing those modules to the fluidic motherboard.

Figure 11:
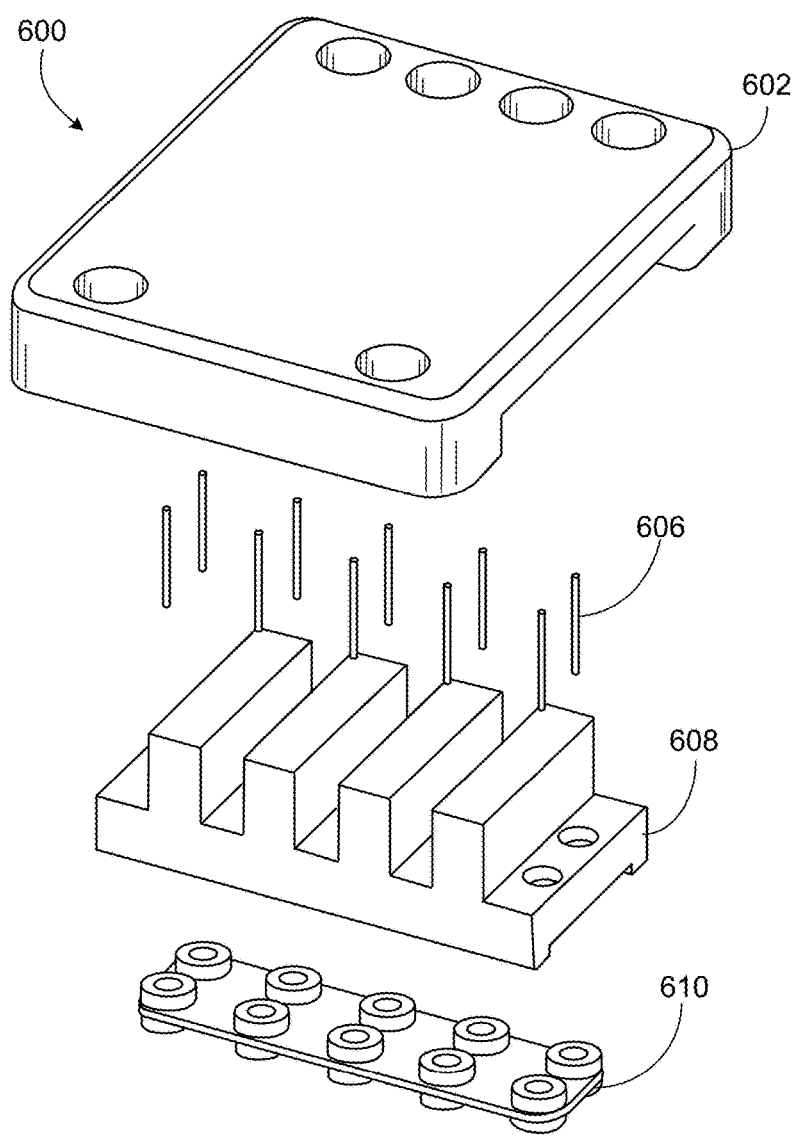
FIG. 11 is an exploded view of the portion of a connection assembly including a housing, tubes, tube holder, and custom gasket.

Turing now to FIG. 11, a connection sub-assembly 600 is illustrated that may be used to establish fluidic communication between conduits and openings or fluidic channels in the fluidic network. In some forms, the fluidic network may not have channels formed therein, but may have various conduits that connect elements or openings on the network to one another. Alternatively, the connection sub-assembly 600 may be used to establish direct fluidic communication between conduits, openings, or fluidic channels formed in a fluid sample processing or analysis module. This sub-assembly 600 includes a housing 602 having a plurality of openings 604, a plurality of tubes 606, a tube holder 608, and a custom gasket 610. The plurality of tubes 606 can be received in the tube holder 608 and extend toward a lower side of the housing 602, and the ends of these plurality of tubes 606 may be placed in fluid communication with external conduits. The bottom ends of the tubes 606 will extend out of the bottom side of the tube holder 608 and into openings in the custom gasket 610. When the custom gasket 610 is compressed between the tube holder 608 and a surface of the network or more specifically a motherboard of the network, the custom gasket 610 forms a seal between each of the plurality of tubes 606 and the network, and places the tubes 606 in fluid communication with openings or channels in the network.

Figure 12A:
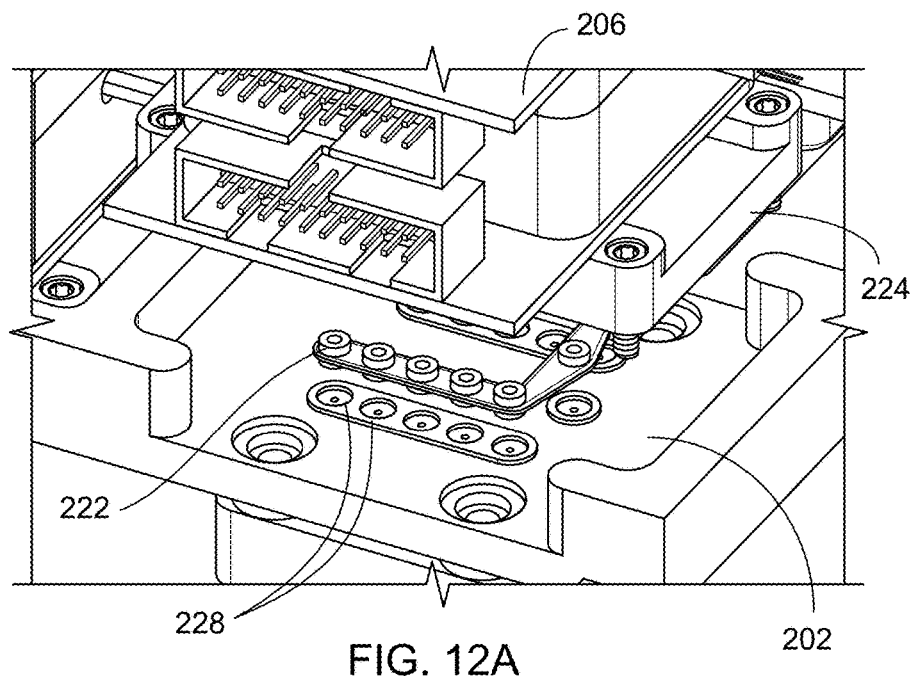
FIG. 12A is a top side partially exploded view of a module separated from the fluidic network to illustrate a gasket disposed therebetween.
Figure 12B:
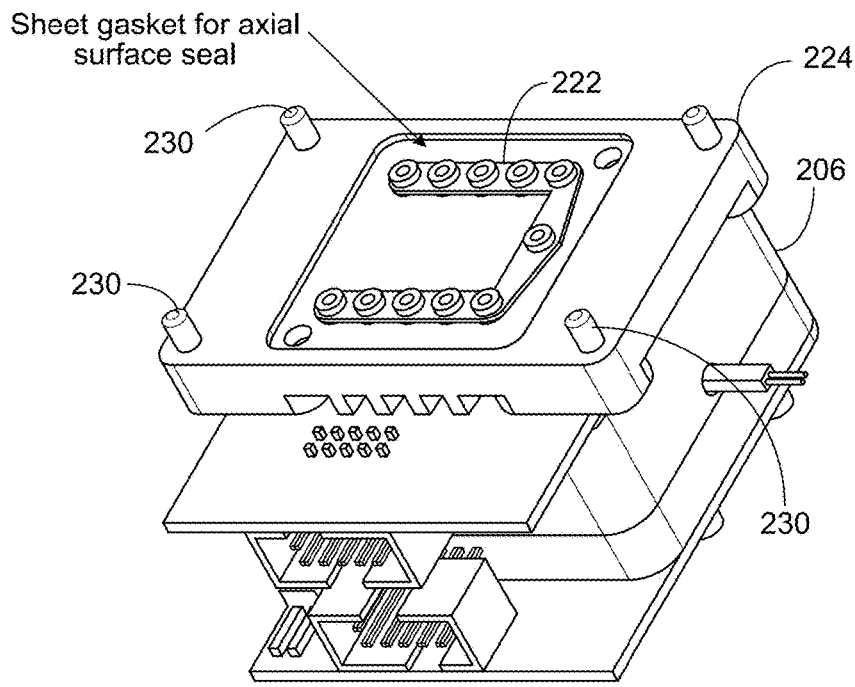
FIG. 12B is a perspective view of a bottom side of a module to illustrate a gasket disposed thereon.
Figure 13:
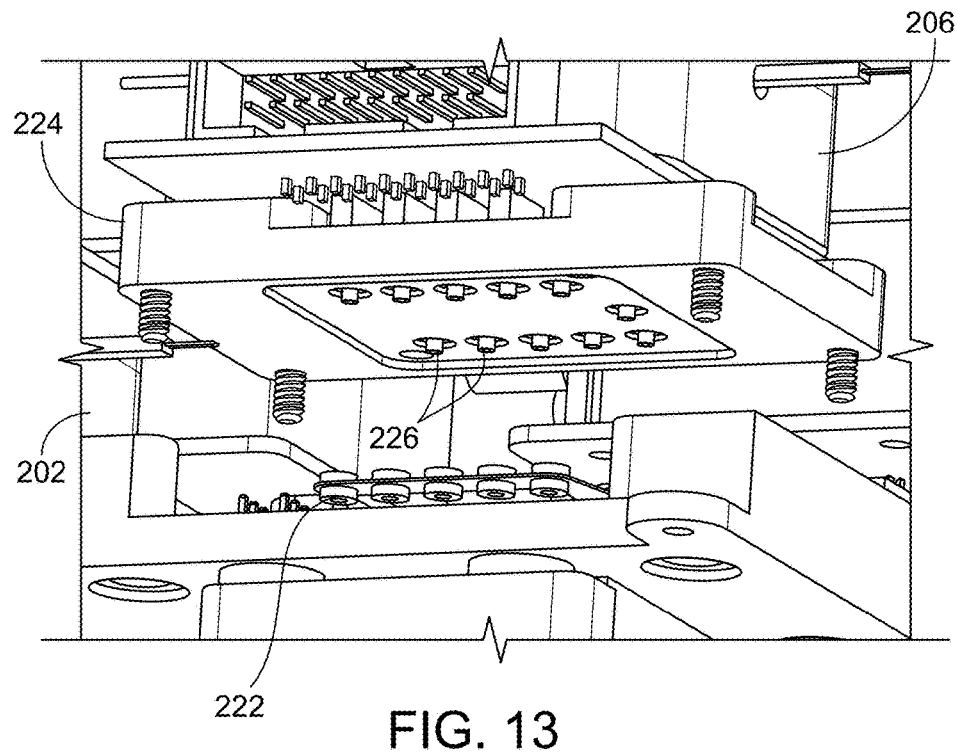
FIG. 13 is a bottom side partially exploded view of the module separated from the network (in an assembly similar to that shown in FIG. 12A) to illustrate the gasket therebetween.
Figure 14:
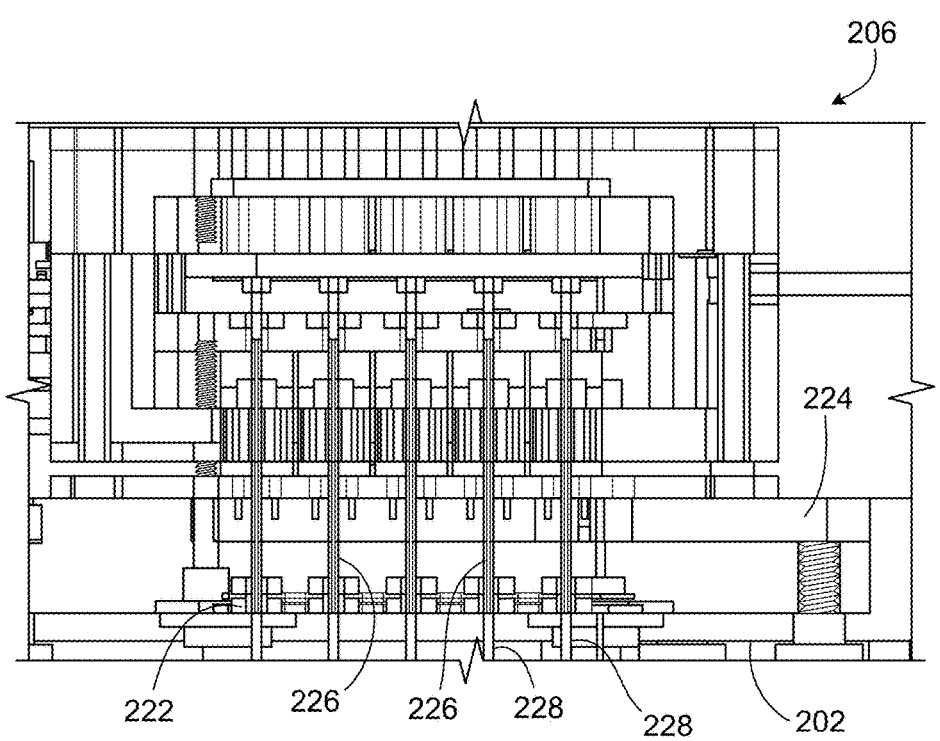
FIG. 14 is a cross-sectional side view taken through a seal area between the module and the network to show how the tubes and gasket place the network and the module in fluid communication with one another.

Turning now to FIGS. 12 through 14, the connection interface for one of the modules 206 shown in FIGS. 6A-6D with the network 202 is illustrated. The connection interface concept shown in FIGS. 12-14 can be used with any of the fluid sample processing modules and the fluid sample analysis modules. In this instance, the customizable gasket 222 and a gasket seat 224 on the underside of the module 206 are interposed between the surface of the network 222 and the underside of the module 206. The plurality of tubes 226 from the module 206 extend through the gasket seat 224 and gasket 222 as is best illustrated in the assembled cross-sectional view of FIG. 14 to connect the fluidic channels 228 in the network 202 to the fluid channel 232 in the integrated photometry chip in the module. As with the other connection sub-assembly 600 that was illustrated, when the module 206 is attached to the network 202, the gasket 222 compresses around the tubes 226 to form a seal between the tubes 226 and the network 202. The tubes 226 do not need to extend into the openings or channels 228 formed in the network, although the tubes 226 can extend for some distance into the module 206 in order to supply the fluid at the channel 232 in the chip. Though FIGS. 12-14 show a connection interface for a photometry module, the same concept may be applied to other modules. For example, in some implementations, the sample processing module (see FIG. 2) can include a gasket arranged in a gasket seat for sealing the actuation input port to a corresponding connector interface on the fluidic mother board that is coupled to the fluid actuation device. Similarly, the sample processing module can include a gasket arranged in a gasket seat for sealing the fluid output port to the fluidic channels 228 in the network 202.

As shown in FIG. 12B, the bottom surface of the module 206 includes multiple protrusions 230 that allow the module 206 to be removably attached to the fluidic motherboard. In the present example, the protrusions 230 are configured to mate with corresponding openings (e.g., to allow the module to achieve an interference fit/frictional fit/press fit with the fluidic motherboard). The connection illustrated is exemplary and not intended to be limiting.

Figure 15A:
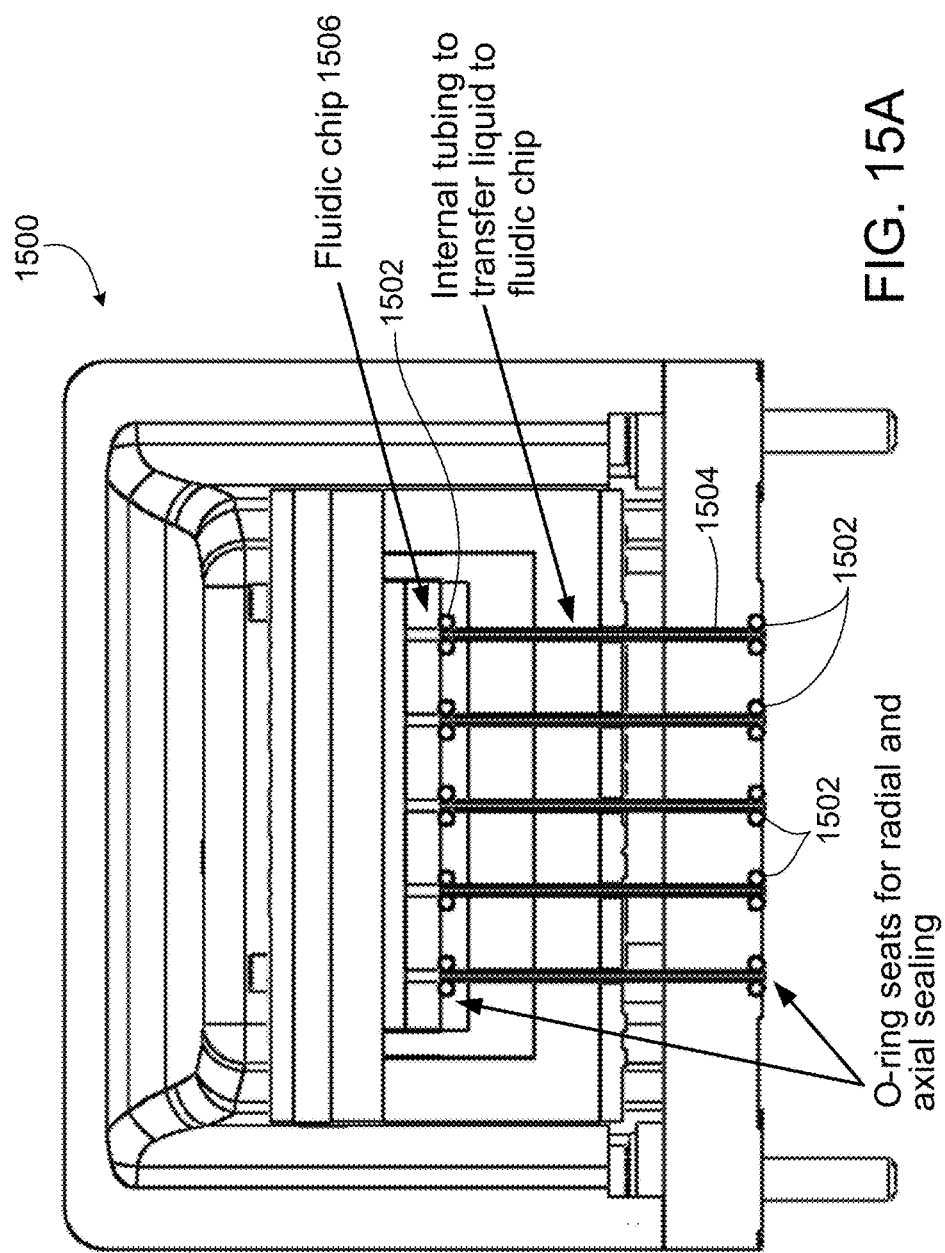
FIG. 15A is a schematic illustrating a cross-section of a technique for forming fluidic seals in an analytical module.
Figure 15B:
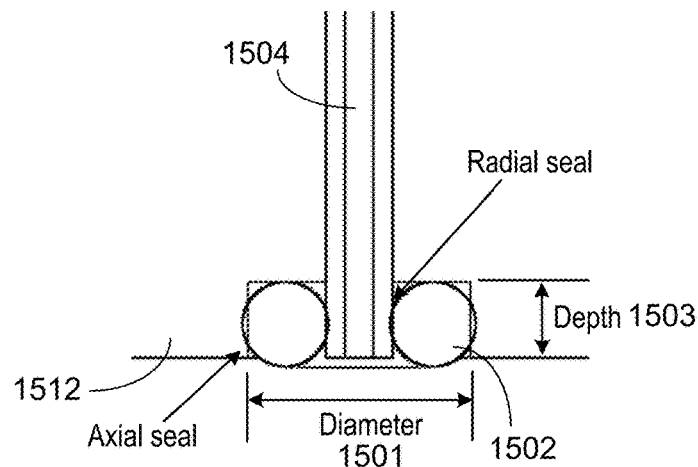
FIG. 15B is a schematic illustrating an O-ring for making axial and radial seals in an analytical module.

FIG. 15A is a schematic illustrating a cross-section of another technique for forming fluidic seals in an analytical module 1500. In this example, O-rings 1502 are used to make seals both axially and radially at the two ends of an internal tube 1504 that is used to transport a fluid sample from a fluid access hole in the fluidic mother board to a region within the module where the analysis of the fluid sample is performed (i.e., fluidic chip 1506 in FIG. 15A). FIG. 15B is a detailed view of the axial and radial seals made by the O-ring 1502. As shown in FIG. 15B, the O-ring 1502 has a defined outer diameter 1501 and is seated in a groove in the O-ring seat 1512 on the underside of the module, in which the O-ring 1502/groove has a fixed depth 1503 in the seat 1512. A tube 1504 located internally within the module passes through the center of the O-ring causing the O-ring elastomer to compress and form a radial seal. The O-ring 1502 also forms a face seal/axial seal with the surface of the fluidic mother board when the module is positioned on the board in the correct seat.

Figure 15C:
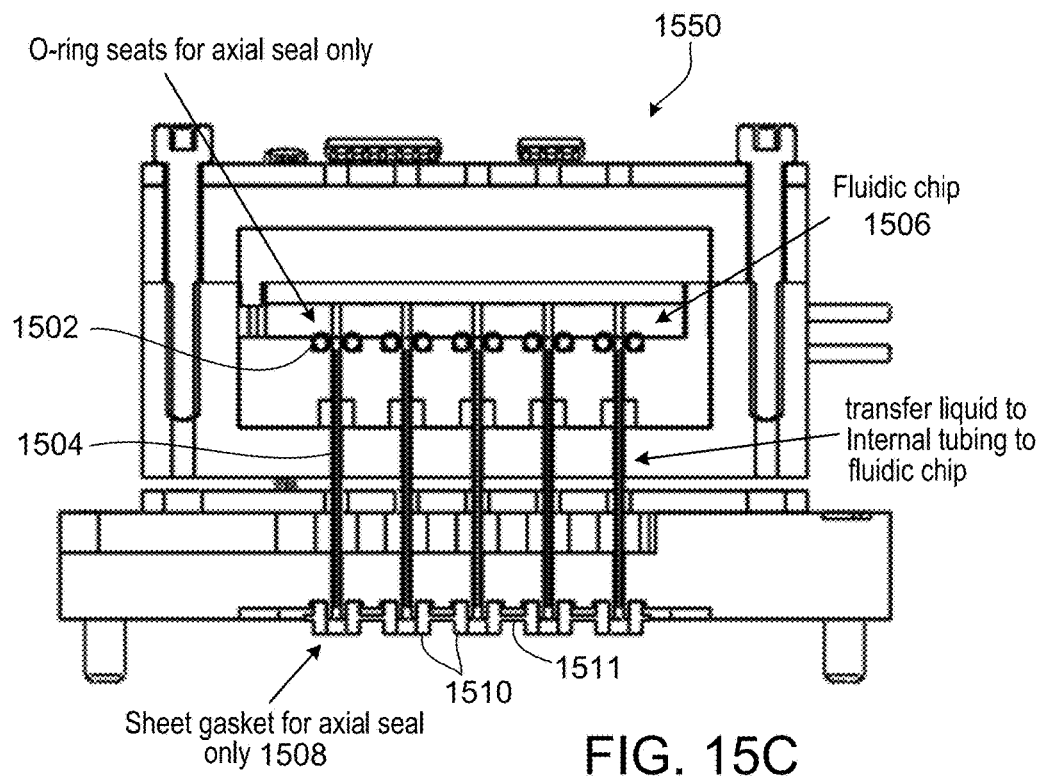
FIG. 15C is a schematic that illustrates a cross section view of a module that utilizes both the gasket seal and O-ring seal.

FIG. 15C is a schematic that illustrates a cross section view of a module 1550 that utilizes both the gasket seal 1508 and O-ring seal 1502. The gasket 1508 is used for creating an axial seal at the interface with the fluidic motherboard and the O-rings 1502 are used to create axial seals between the internal tubing 1504 and the fluidic chip 1506 within the module. FIG. 15D shows a detailed view of the gasket seal 1508. The gasket 1508 includes multiple sealing rings 1510 that form the axial seal between the tubing and the fluidic motherboard. The depth and diameter of the sealing rings 1510 are important for creating the seal. Additionally, a thin membrane 1511 connects all of the sealing rings 1510 so that they form the single sheet gasket 1508.

Figure 16:
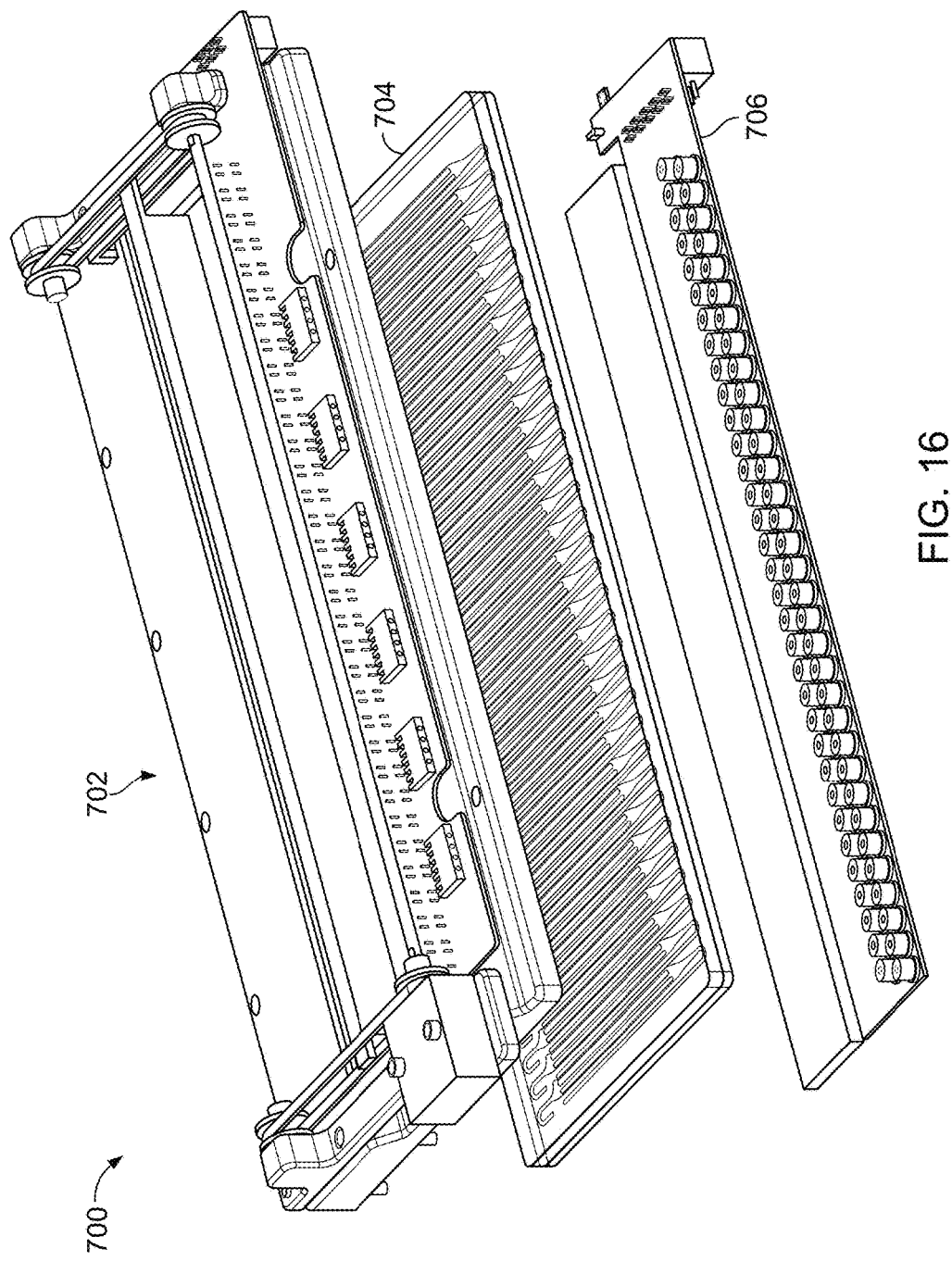
FIG. 16 is an exploded perspective view of the mixing system module detached from the fluidic network.

FIG. 16 illustrates the internal components of a mix and incubate module 700 (that may be similar or identical to the mix and incubate module 204) including a housing and actuator 702, mixing channels 704, and flow sensors 706. This module can also include a heater in order to provide incubation of the samples being tested. The mix and incubate module helps to minimize cost per test and maximize assay menu flexibility by providing a space for mixing and incubating assays with temperature control.

Figure 17A:
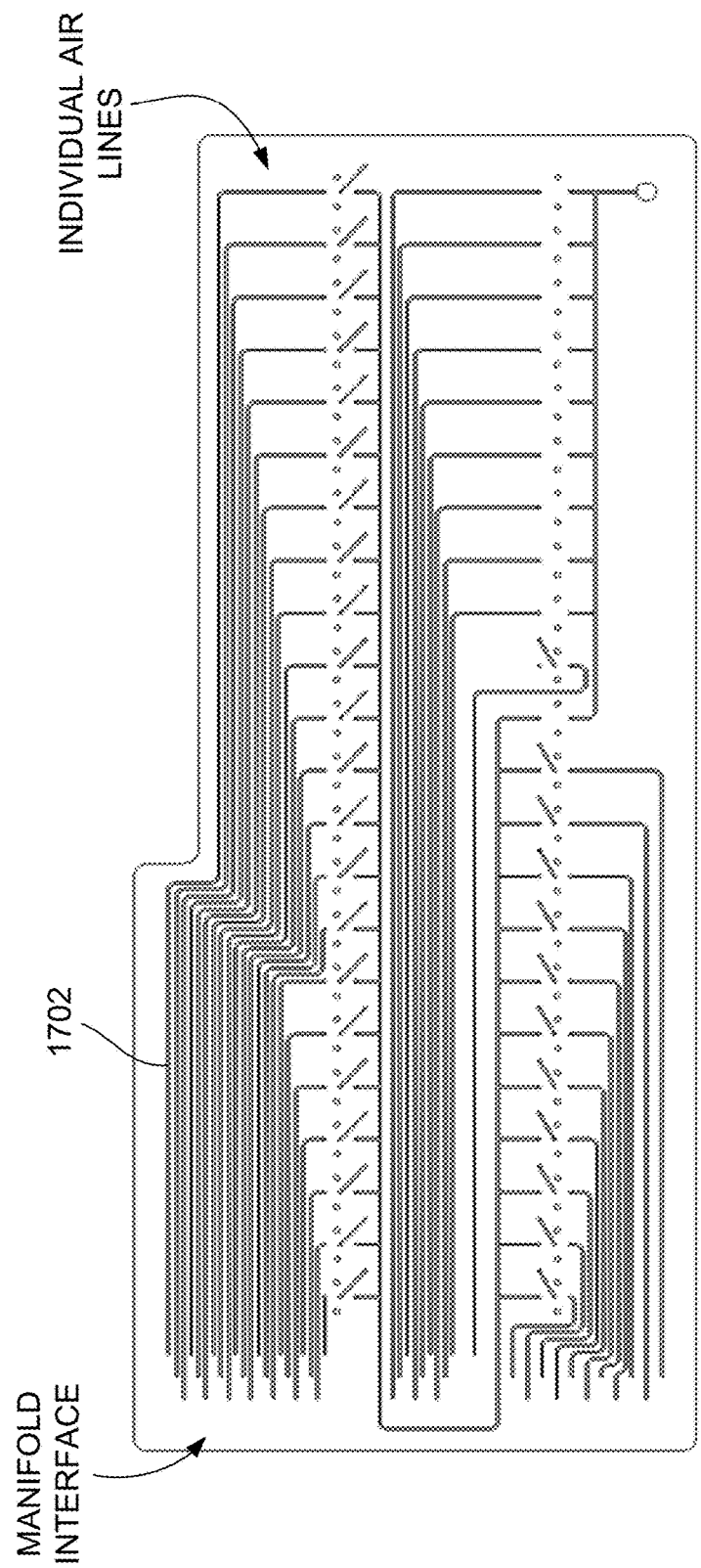
FIG. 17A is a schematic illustration of the pneumatic control system.
Figure 17B:
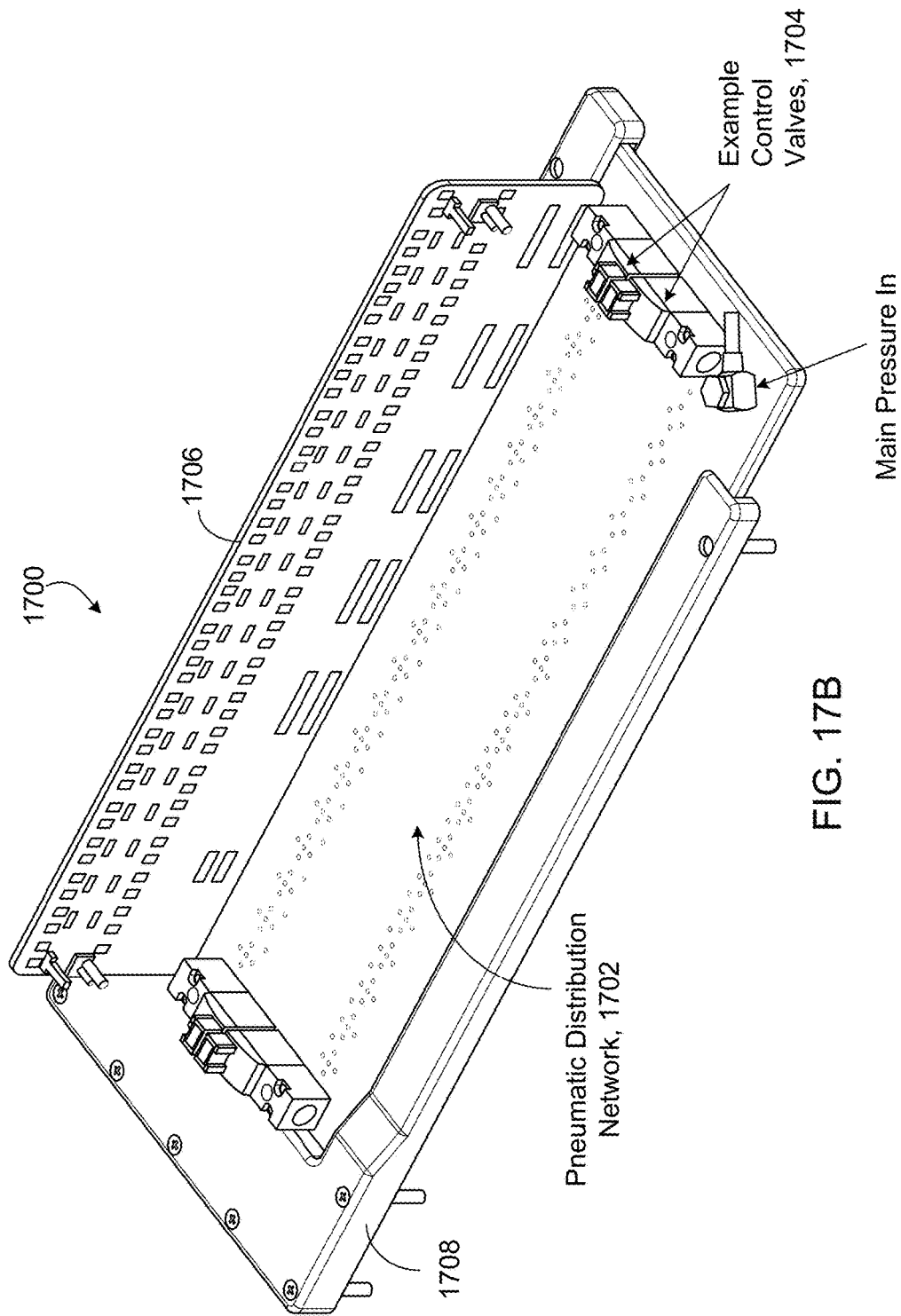
FIG. 17B is a schematic illustrating a perspective view of the entire pneumatic module.

FIG. 17A illustrates a pneumatic control system routing board/distribution network 1702. This board 1702 can be configured to pneumatically transport the fluid samples through various individual assay lines or all of the lines at a system level by proper configuration of the various switches. FIG. 17B is a schematic illustrating a perspective view of the entire pneumatic module 1700 including examples of valves 1704, the pneumatic distribution network 1702, the electronics control board 1706, and the module housing 1708.

Figure 20:
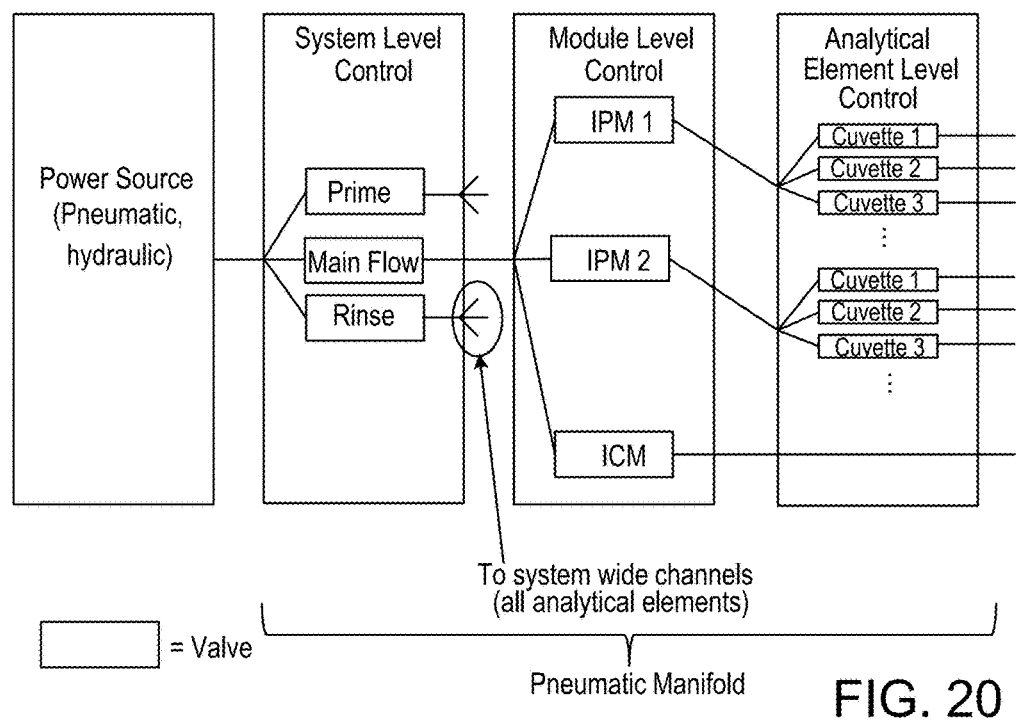
FIGS. 20 through 22 are high-level schematics that show various embodiments of the valving for a hydraulic or pneumatic control system.
Figure 21:
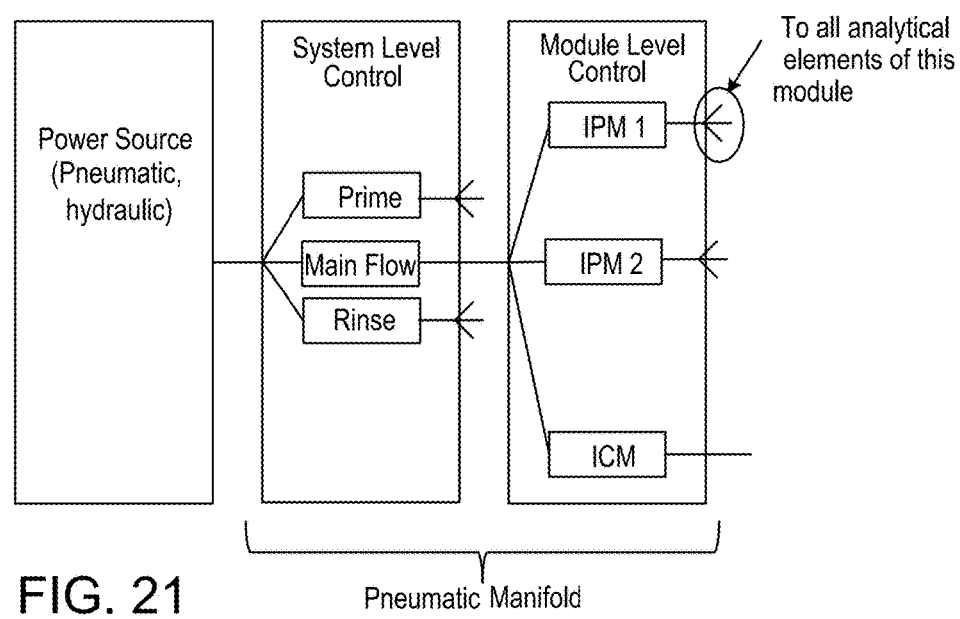
Figure 22:
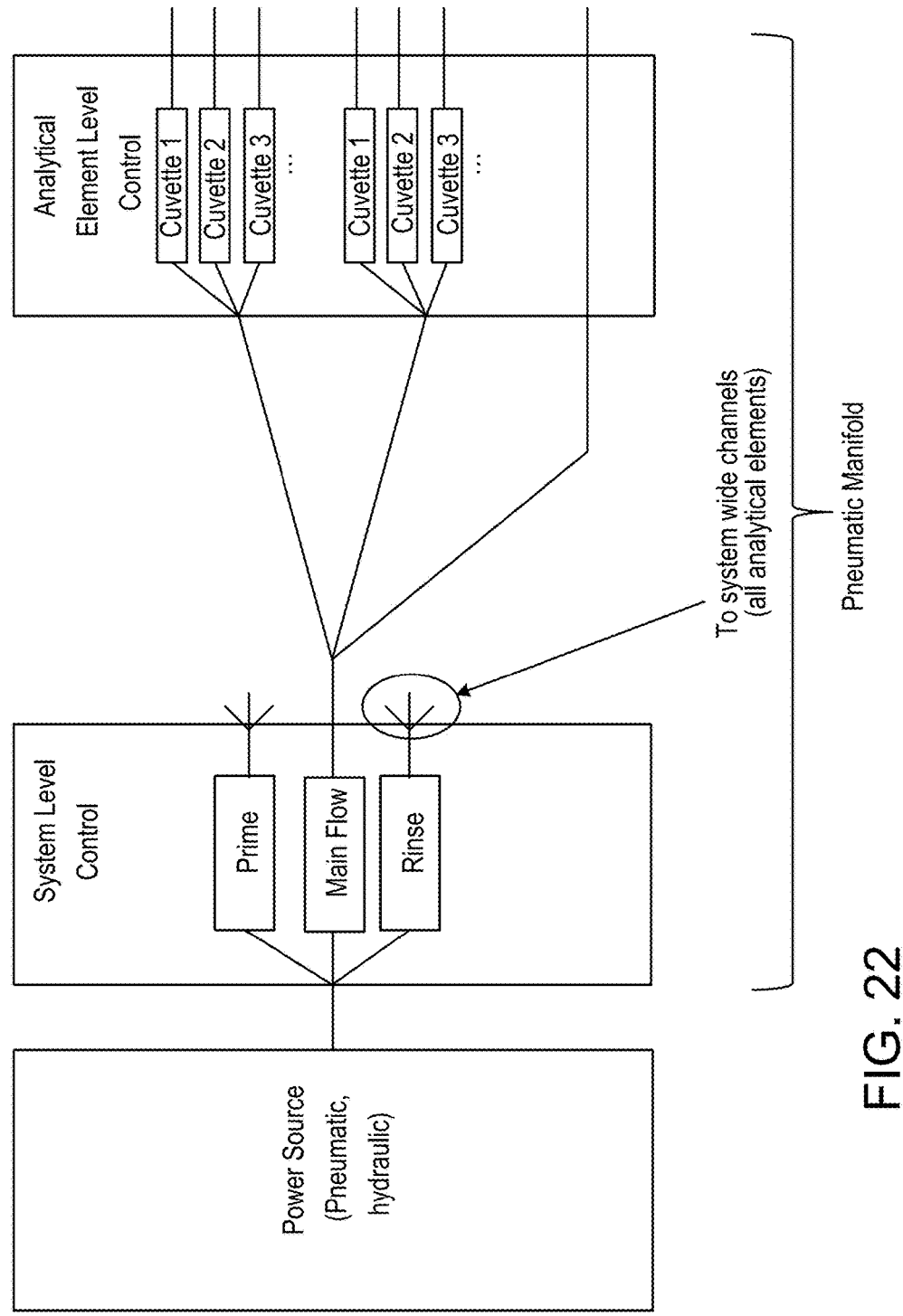

With additional forward reference to FIGS. 20 to 22, the fluid connectivity of a power source for transport (such as a pneumatic or hydraulic control system) is illustrated. In each of FIGS. 20 to 22, small rectangles are used to indicate valved items, although the larger rectangles are used to generally indicate and group the system level, the module level, and the intra-module level features.

Looking first at FIG. 20, it can be seen that the power source is connected to various system level control features including a valve for providing fluid (either liquid or gas) to perform a prime function and a valve for providing fluid to perform a rinse function. As indicated in the figure annotation, the branched channel architecture indicates that the valved line connects to system wide channels (that is, to all analytical elements). There is also a main flow valve at the system level control that selectively connects the hydraulic or pneumatic power source to the various module level controls. In the form illustrated, when the main flow valve is opened, it places the power source in fluid communication with the IPM1 valve, the IPM2 valve, and the ICM valve via respective fluid lines. Each of the valves illustrated in FIG. 20 may be formed on the pneumatic manifold. Although valves for three modules are illustrated, it is contemplated that there could be valves to separately regulate flow to any number of modules. Each of the IPM1 valve, the IPM2 valve, and the ICM valve may be independently operated to provide fluid and control fluid flow to the respective module. Still yet, when one or more of the module level control valves are open, a fluid is supplied to the respective module(s) and there may be additional valves within each module that separately control flow to the intra-module components, such as cuvettes 1, 2, and 3 in the IPM modules. However, it is contemplated that for some modules, such as the ICM, it may not be necessary to have intra-module valving. The output flow at the far right end of the schematic may then be disposed of or redirected into the system, depending of the particular function being performed.

By control of these various valves at different levels (system, module, intra-module), the system may be selectively controlled to regulate the flow of fluid into the various parts of the fluidic network and the attached modules for testing of the fluid. Control of the various valves may be directed by software or testing or diagnostic programs, but there may also be ways for a user to discretely control the valves for maintenance or by programming the device.

Turning now to FIG. 21, an alternative schematic is provided illustrating the hydraulic or pneumatic architecture of the fluidic network. In this example, there are only valved controls available at the system level (for example, prime, main flow, and rinse) and at the module level (for example, IPM1, IPM2, and ICM). In the particular illustrated embodiment in FIG. 21, there is not discretely valved control of intra-module elements such as cuvettes as with the embodiment illustrated in FIG. 20. Thus, for example, if flow to IPM1 is turned on, all of the cuvettes in IPM1 receive this fluid flow.

Alternatively, the module level controls might be eliminated as illustrated in the embodiment of FIG. 22. In this embodiment, there are system level valved controls (prime, main flow, and rinse) and intra-module level valved controls or analytical element level controls (cuvettes 1, 2, and 3). In this arrangement, there are not intermediate module level valved controls for separately regulating flow into the various modules.

The systems illustrated in FIGS. 20 to 22 are intended to be illustrative of some hydraulic or pneumatic systems, but should not be considered as the only possible ways to control hydraulic or pneumatic flow of a fluid. Other variations, for example, the addition or removal of valving at different levels of the system, are contemplated.

Figure 18A:
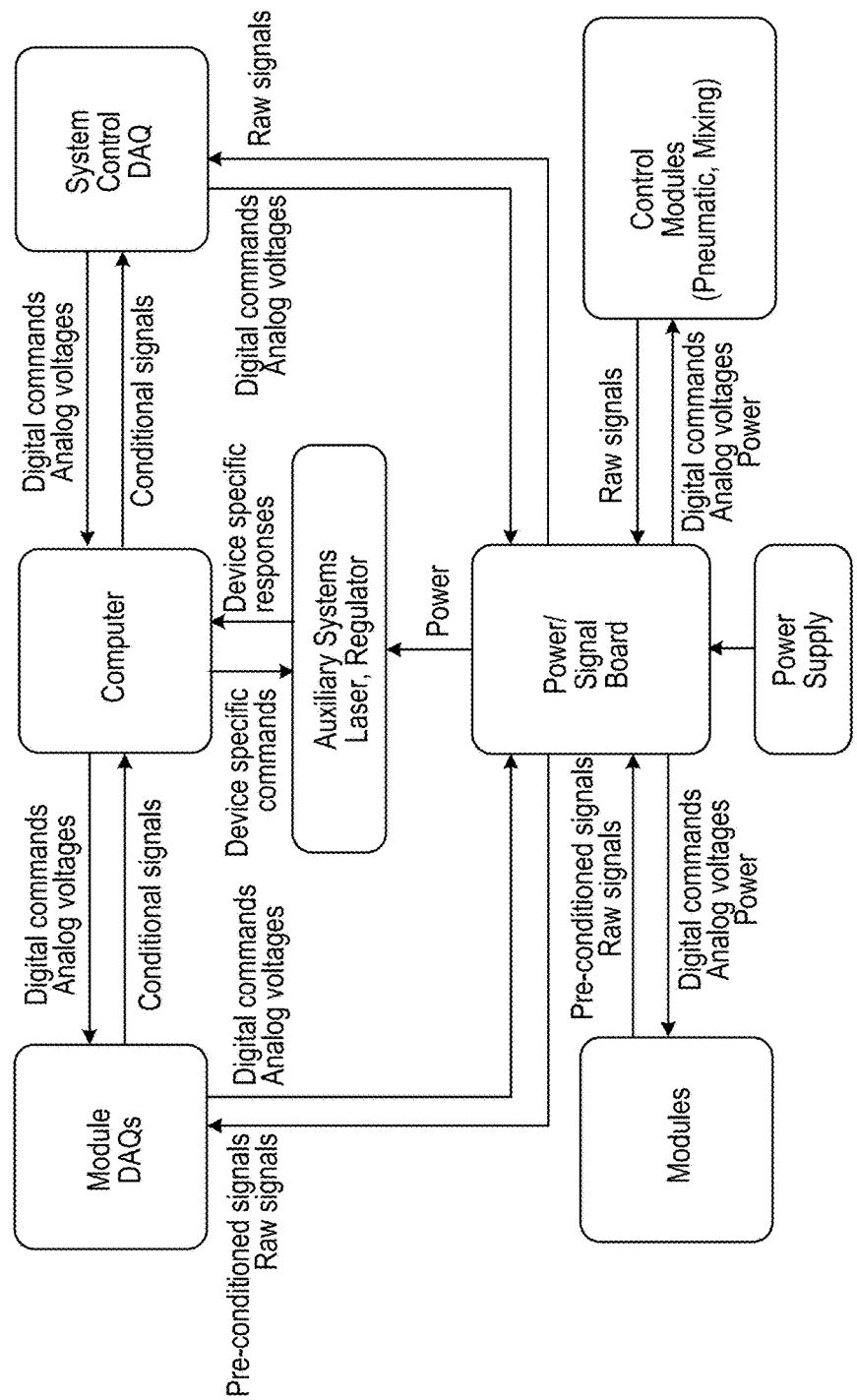
FIG. 18A is a schematic illustration of the electronic control system of a modular analytic system.

Turning now to FIG. 18A, the setup of the electronic system for a modular analytic system is illustrated schematically. Various system elements are illustrated in the boxes [e.g., the power supply, the power/signal board or controller, the modules, the control modules for pneumatic control and mixing, the auxiliary systems such as lasers and pressure regulators, a computer, and data acquisition (DAQ) equipment for the modules and system control]. The sharing or electrical communication of signals or power is indicated by the arrows linking the boxes.

For example, power is supplied by the power supply to the power/signal board. The power signal board supplies this power to the modules for detection and analysis of the samples, the modules for pneumatic and mixing control, and the auxiliary systems. It is contemplated that the DAQ equipment and the computer may be separately powered.

In terms of system control, the computer passes digital commands and analog voltages to the DAQ equipment which may be passed to the power/signal board or central controller. The power/signal board can then pass these digital commands and analog voltages to the detector modules and the control modules to perform their appropriate operations. The detector modules can return pre-conditioned signals and raw signals to the power/signal board and the control modules can pass raw signals back to the power/signal board. The power/signal board can then send pre-conditioned and raw signals to the DAQ for the detector modules and send the raw signals from the control modules back to the DAQ for the system control elements. The DAQ devices can then send conditioned signals back to the computer. In the setup illustrated, the computer and the auxiliary systems are able to pass device specific command and responses back and forth with one another.

It should be appreciated that the digital commands, analog voltages, raw signals, pre-conditioned signals, and conditioned signals may be passed through some of the equipment (e.g., the DAQ equipment or the power/signal board) or may be processed and appropriately converted along the way. Whether additional signal processing may occur will depend on the capabilities and configuration of the various hardware elements in the setup.

It is separately noted that in some instances the DAQ equipment might be integrated with the power/signal board or provided as a card or the like that can be installed in and implemented in the computer.

Thus, it will be readily appreciated that the system setup of FIG. 18A is illustrative, but not intended to be limiting, as there are variations that could be made to this setup by one having ordinary skill in the art without deviating from the modular aspects of the system of this disclosure.

Figure 18B:
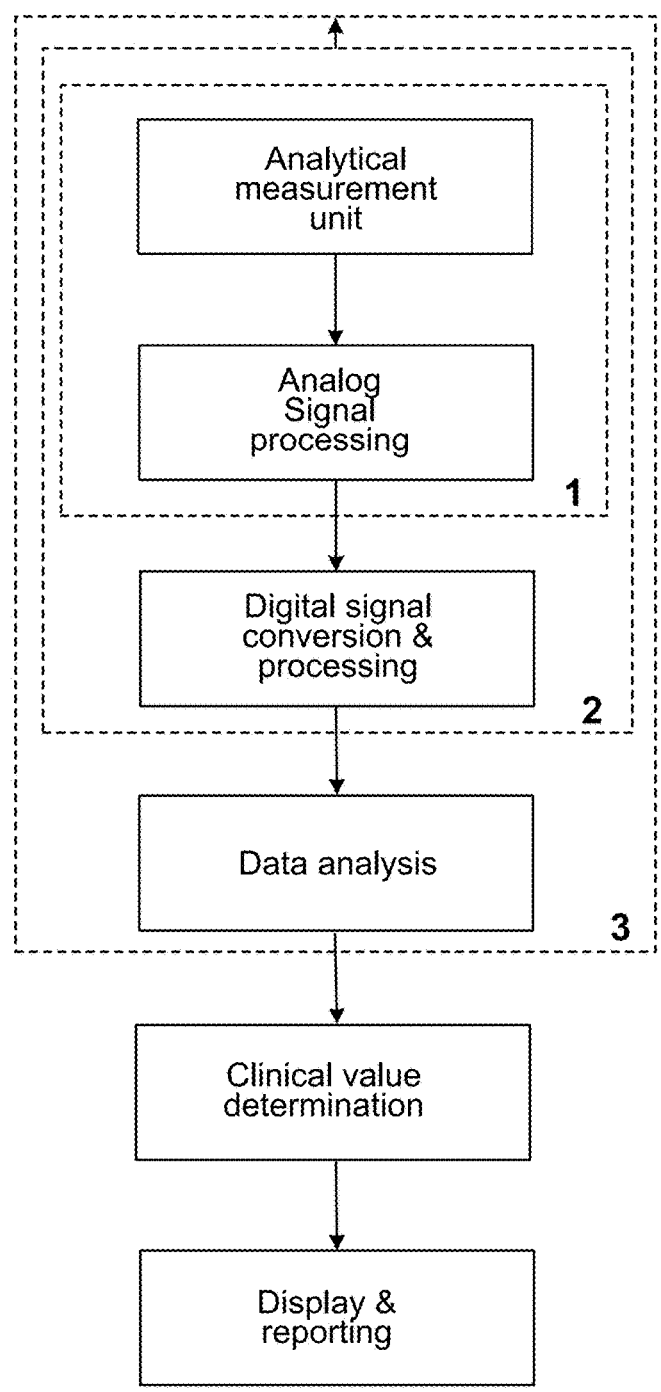
FIG. 18B is a block diagram illustrating an overview of the different levels of data acquisition, processing and analysis that may be performed by one or more analytical modules.

As explained herein, each analytical module may perform various levels of signal conditioning and analysis before measurement signals are transmitted from the module to the control electronics for further processing and analysis. FIG. 18B is an overview of several different levels of data acquisition, processing and analysis that may be performed by one or more analytical modules coupled to the fluidic motherboard. The different levels of operations are denoted as "1," "2," and "3," and may overlap. In a first example configuration, a module only does basic analog signal processing (e.g., amplifying measurement signals, current to voltage conversion, filtering, among other basic analog signal processing) before passing the measurement signal to the central processing unit. In a second example configuration, the module additionally performs digital signal processing (e.g., conversion of an analog measurement signal to a digital measurement signal, addition or subtraction of digital signals, digital filtering) before passing the measurement signal to the central processing unit. In a third example configuration, the module also performs signal analysis that may be necessary to generate data that is useful for clinical evaluation purposes (e.g., identification of signal peak values or identification of temporal signal properties such as frequency or period). The output in this case can be passed directly into the CPU for conversion to a clinical value in software before reporting (e.g., being output to a display or saved in memory).

Figure 19:
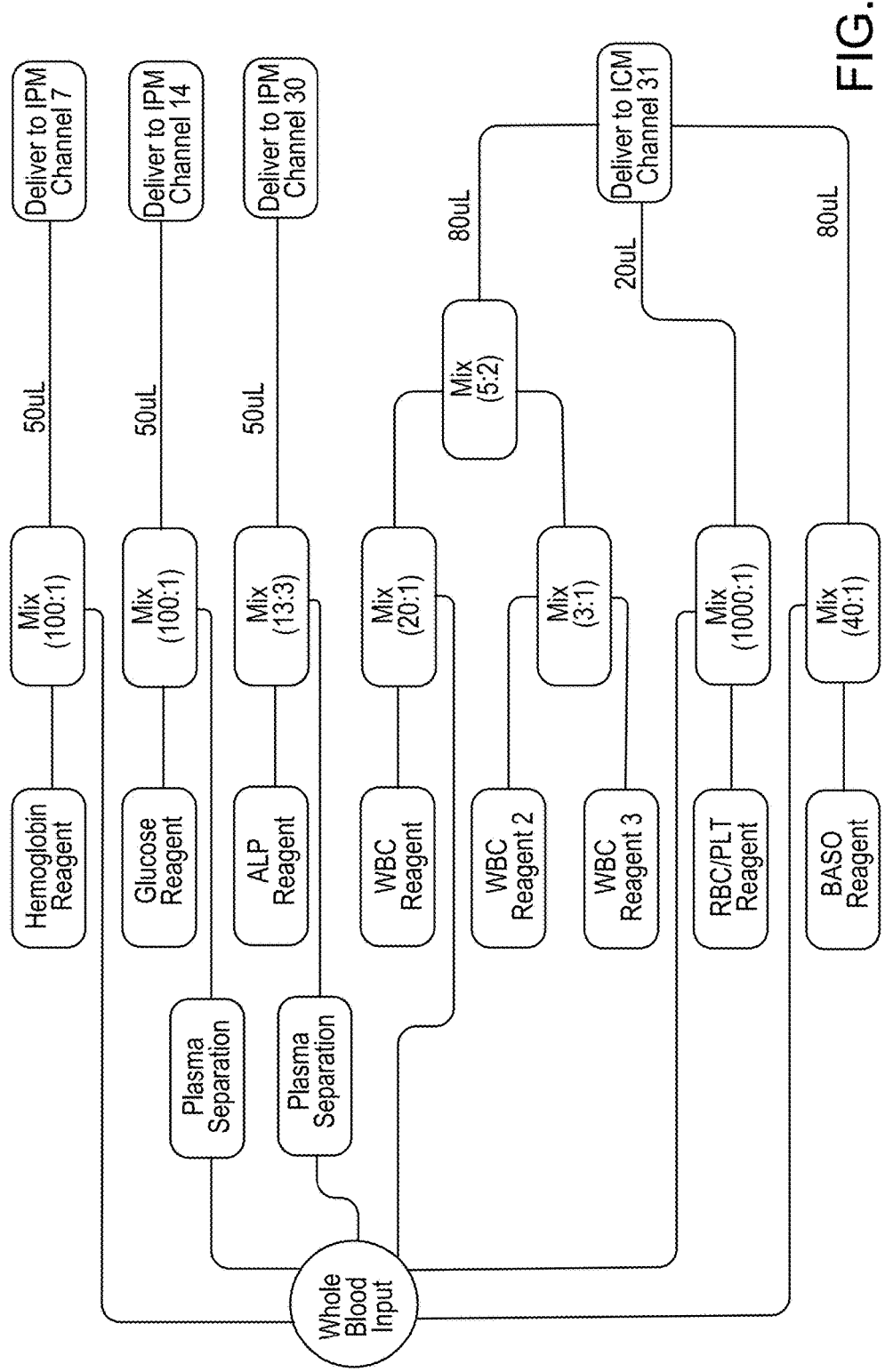
FIG. 19 is a schematic illustrating the sample processing that may be performed using the modular analytic system.

Turning to FIG. 19, a sample processing schematic is provided for processing of a whole blood input according to one aspect of use of the modular system. This illustration shows how a single sample may be split and routed a number of different ways to perform simultaneous testing of the same.

As illustrated, the whole blood input is provided from the sample processing system into the modular analytic system. The whole blood input is split six ways into six different conduits. A first portion of the whole blood is mixed with a hemoglobin reagent in a 100:1 ratio and 50 microliters is provided to one of the integrated photometry modules for processing. A second portion of the whole blood undergoes plasma separation and this then mixed in a 100:1 ratio with a glucose reagent before 50 microliters is provided to one of the integrated photometry modules for processing. A third portion of the whole blood also undergoes plasma separation and is mixed with an alkaline phosphatase (ALP) reagent in a 13:3 ratio before providing 50 microliters of the sample to one of the integrated photometry modules for processing. A fourth portion of the whole blood is mixed with a first white blood cell (WBC) reagent in a 20:1 ratio and is mixed in a 5:2 ratio with a second and a third WBC reagents that have been mixed in a 3:1 ratio; 80 microliters of this sample is then delivered to the integrated cytometry module. A fifth portion of the whole blood is mixed in a 1000:1 ratio with a red blood cell/platelet (RBC/PLT) reagent and 20 microliters is supplied to the integrated cytometry module. A sixth portion of the whole blood is mixed with a basophil (BASO) reagent in at a 40:1 ratio and 80 microliters is supplied to the integrated cytometry module.

Other Embodiments

A number of embodiments have been described. Nevertheless, it will be understood that various modifications may be made without departing from the spirit and scope of the invention. Other embodiments are within the scope of the following claims.

We claim:

1. A modular analytic system comprising:
a base;
at least one fluid sample processing module configured to be removably attached to the base;
at least one fluid sample analysis module configured to be removably attached to the base;
a fluid actuation module positioned on the base;
a fluidic network comprising a plurality of fluidic channels, wherein the fluid actuation module is arranged to control transport of a fluid sample between the at least one sample processing module and the at least one sample analysis module through the fluidic network,
wherein each fluid sample processing module and each fluid sample analysis module comprises a corresponding internal fluidic chip,
wherein each fluid sample processing module and each fluid sample analysis module comprises a corresponding plurality of tubes extending from the internal fluidic chip and out of the module to the base, at least one tube of the plurality of tubes for each module is arranged to receive a fluid sample from the fluidic network to the internal fluidic chip and at least one other tube of the plurality of tubes for each module is arranged to deliver a fluid sample from the internal fluidic chip to the fluidic network when the module is attached to the base,
wherein an underside of each fluid sample processing module and each fluid sample analysis module comprises a plurality of recesses facing the base, each recess comprising a hole through which a respective tube from the plurality of tubes extends,
wherein each fluid sample processing module and each fluid sample analysis module comprises
a corresponding first fluidic seal that forms a sealed pathway between the plurality of tubes extending out of the module and the fluidic channels of the fluidic network, each first fluidic seal comprising a gasket having a plurality of sealing rings that seat within the plurality of recesses, respectively, wherein each sealing ring of the plurality of sealing rings comprises a thickness that is greater than a depth of the recess within which the sealing ring sits, and
a corresponding second fluidic seal that is internal to the module and provides a fluidic seal between the internal fluidic chip and the plurality of tubes; and
an electronic processor, wherein the electronic processor is configured to control operation of the fluid actuation module and receive measurement data from the at least one fluid sample analysis module.

2. The modular analytic system of claim 1, further comprising a cartridge, wherein the cartridge comprises:
one or more first receptacles configured to store a fluid sample;
one or more second receptacles configured to store one or more reagents; and
a third receptacle, wherein
the fluid sample processing module comprises an opening to receive the cartridge,
wherein the sample processing module further comprises an actuation input port and a fluid output port, wherein the actuation input port and the fluid output port are arranged to couple to the third receptacle of the cartridge when the cartridge is positioned in the opening of the sample processing module.

3. The modular analytic system of claim 2, wherein the base comprises a first connector interface coupled to the fluid actuation module, and wherein the actuation input port of the sample processing module is configured to mate with the first connector interface.

4. The modular analytic system of claim 3, wherein the board comprises a fluidic connector interface coupled to the fluidic network, and wherein the fluid output port of the sample processing module is configured to mate with the fluidic connector interface.

5. The modular analytic system of claim 1, wherein the at least one fluid sample analysis module comprises a light detector module, an electrochemistry module, a cytometry module, or a Coulter counter module.

6. The modular analytic system of claim 1, comprising a plurality of the fluid sample analysis modules removably attached to the base, wherein at least one fluid sample analysis module is arranged to deliver a fluid sample through the fluidic network to at least one other fluid sample analysis module.

7. The modular analytic system of claim 1, wherein the fluid actuation module comprises a compressed gas or hydraulic source to supply pressure to the fluidic network, wherein the fluid actuation module comprises a manifold that separates the pressure supplied by the fluid actuation module into a plurality of independent channels, wherein the fluid actuation module comprises a plurality of valves, and wherein the electronic processor is operable to control the operation of the plurality of valves.

8. The modular analytic system of claim 1, wherein the fluid actuation module is removably attached to the base, wherein the fluid actuation module comprises one or more protrusions or openings, and wherein, for each protrusion or opening on the fluid actuation module, the base comprises a corresponding opening or protrusion that frictionally fits to the protrusion or opening.

9. The modular analytic system of claim 1, further comprising a waste module configured to be removably attached to the base, wherein the waste module comprises a fluidic connector interface that mates with one or more of the fluidic channels, wherein the waste module comprises one or more protrusions or openings, wherein, for each protrusion or opening on the waste module, the base comprises a corresponding opening or protrusion that frictionally fits to the protrusion or opening, and wherein the fluidic actuation module is operable to control the flow of fluid samples from the at least one analytic module to the waste module.

10. The modular analytic system of claim 1, wherein the fluidic channels are formed in the base or comprise a plurality of tubes.

11. The modular analytic system of claim 1,
wherein each sealing ring of the plurality of sealing rings comprises an outer diameter that is as wide as a diameter of the recess within which the sealing ring sits,
wherein each sealing ring of the plurality of sealing rings comprises an inner diameter corresponding to a hole within the sealing ring, and
wherein the inner diameter is as wide as an outer diameter of a tube that extends through the hole within the sealing ring.

12. The modular analytic system of claim 11, wherein the plurality of sealing rings are connected by a membrane having a thickness that is less than the thickness of the sealing rings.

* * * * *